(12) United States Patent
Gauthier et al.

(10) Patent No.: US 7,407,959 B2
(45) Date of Patent: *Aug. 5, 2008

(54) CATHEPSIN CYSTEINE PROTEASE INHIBITORS

(75) Inventors: Jacques Yves Gauthier, Laval des Rapides (CA); Chun Sing Li, Dollard-des-Ormeaux (CA); Christophe Mellon, L'Ile Bizard (CA)

(73) Assignee: Merck Frosst Canada & Co., Quebec (CA)

(*) Notice: Subject to any disclaimer, the term of this patent is extended or adjusted under 35 U.S.C. 154(b) by 235 days.

This patent is subject to a terminal disclaimer.

(21) Appl. No.: 11/282,536

(22) Filed: Nov. 18, 2005

(65) Prior Publication Data

US 2006/0111440 A1 May 25, 2006

Related U.S. Application Data

(60) Provisional application No. 60/630,405, filed on Nov. 23, 2004.

(51) Int. Cl.
*A61K 31/497* (2006.01)
*A61K 31/425* (2006.01)
*C07D 241/04* (2006.01)
*C07D 211/84* (2006.01)
*C07D 277/30* (2006.01)

(52) U.S. Cl. .................. 514/252.1; 514/357; 514/365; 544/393; 544/400; 546/300; 548/204; 548/205; 558/404; 558/414; 558/431; 558/434

(58) Field of Classification Search .............. 514/252.1, 514/357, 365, 396, 521; 544/393, 400; 546/330; 548/204, 205; 558/404, 414, 431, 434
See application file for complete search history.

(56) References Cited

U.S. PATENT DOCUMENTS

2003/0232863 A1 12/2003 Bayly et al.
2005/0014941 A1* 1/2005 Black et al. ................. 544/163
2005/0182096 A1* 8/2005 Link et al. ................... 514/317
2005/0240023 A1* 10/2005 Bayly et al. ................. 546/330

FOREIGN PATENT DOCUMENTS

| CA | 2 439 415 | 9/2002 |
| WO | WO 99/24460 | 5/1999 |
| WO | WO 03/075836 | 9/2003 |

OTHER PUBLICATIONS

Alessandro Volonterio, et al. "Synthesis of Partially Modified Retro and Retroinverso [NHCH(CF3)]-Peptides," Organic Letters 2000, vol. 2, No. 13, 1827-1830.
Alessandro Volonterio, et al. "Solution/solid-phase synthesis of partially modified retro-[NHCH(CF3)]-peptidyl hydroxamates," Tetrahedron Letters 42 (2001), 3141-3144.
Alessandro Volonterio, et al. "Solid-phase synthesis of partially-modified retro and retro-inverso [NHCH(CF3)]-peptides," Tetrahedron Letters 41 (2000) 6517-6521.
Ishii, et al. "Asymmetric Addition Reactions of Grignard Reagents to Chiral Fluoral Hemiacetal: Asymmetric Synthesis of 1-Substituted-2,2,2,-Trifluoroethylamines," Synlett, Dec. 1997, 1381-1382.
Ishii, et al. "Stereospecific Reduction with Retention of Chiral Fluoral-derived 1,3-Oxazolidines with LiAlH4: Asymmetric Synthesis of 1-Substituted 2,2,2-Trifluoroethylamines," Chem. Letters 1998, 119-120.
Robichaud, J et al., Biorganic & Medicinal Chemistry Letters 14, pp. 4291-4295 (2004), "Rational design of potent and selective NH-linked aryl/heteroaryl cathepsin K inhibitors".

* cited by examiner

*Primary Examiner*—James O. Wilson
*Assistant Examiner*—Ebenezer Sackey
(74) *Attorney, Agent, or Firm*—Nicole M. Beeler; David A. Muthard

(57) ABSTRACT

This invention relates to a novel class of compounds which are cysteine protease inhibitors, including but not limited to, inhibitors of cathepsins K, L, S and B. These compounds are useful for treating diseases in which inhibition of bone resorption is indicated, such as osteoporosis.

9 Claims, No Drawings

CATHEPSIN CYSTEINE PROTEASE INHIBITORS

PRIORITY CLAIM

This application claims priority to U.S. Provisional Application Ser. No. 60/630,405, filed Nov. 23, 2004.

BACKGROUND OF THE INVENTION

A variety of disorders in humans and other mammals involve or are associated with abnormal bone resorption. Such disorders include, but are not limited to, osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, hypercalcemia of malignancy or multiple myeloma. One of the most common of these disorders is osteoporosis, which in its most frequent manifestation occurs in postmenopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. As many as 50% of women and a third of men will experience an osteoporotic fracture. A large segment of the older population already has low bone density and a high risk of fractures. There is a significant need to both prevent and treat osteoporosis and other conditions associated with bone resorption. Because osteoporosis, as well as other disorders associated with bone loss, are generally chronic conditions, it is believed that appropriate therapy will typically require chronic treatment.

Cathepsins belong to the papain superfamily of cysteine proteases. These proteases function in the normal physiological as well as pathological degradation of connective tissue. Cathepsins play a major role in intracellular protein degradation and turnover and remodeling. To date, a number of cathepsin have been identified and sequenced from a number of sources. These cathepsins are naturally found in a wide variety of tissues. For example, cathepsin B, C, F, H, L, K, O, S, V, W, and Z have been cloned. Cathepsin L is implicated in normal lysosomal proteolysis as well as several diseases states, including, but not limited to, metastasis of melanomas. Cathepsin S is implicated in Alzheimer's disease, atherosclerosis, chronic obstructive pulmonary disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immune responses, including, but not limited to, rejection of organ transplants or tissue grafts. Increased Cathepsin B levels and redistribution of the enzyme are found in tumors, suggesting a role in tumor invasion and metastasis. In addition, aberrant Cathepsin B activity is implicated in such disease states as rheumatoid arthritis, osteoarthritis, pneumocystisis carinii, acute pancreatitis, inflammatory airway disease and bone and joint disorders.

Mammalian cathepsins are related to the papain-like cysteine proteases expressed by disease-causing parasites including those from the families protozoa, platyhelminthes, nematodes and arthropodes. These cysteine proteases play an essential role in the life cycle of these organisms.

Human type I collagen, the major collagen in bone is a good substrate for cathepsin K. See Kafienah, W., et al., 1998, *Biochem J* 331:727-732, which is hereby incorporated by reference in its entirety. In vitro experiments using antisense oligonucleotides to cathepsin K, have shown diminished bone resorption in vitro, which is probably due to a reduction in translation of cathepsin K mRNA. See Inui, T., et al., 1997, *J Biol Chem* 272:8109-8112, which is hereby incorporated by reference in its entirety. The crystal structure of cathepsin K has been resolved. See McGrath, M. E., et al., 1997, *Nat Struct Biol* 4:105-109; Zhao, B., et al., 1997, *Nat Struct Biol* 4:109-11, which are hereby incorporated by reference in their entirety. Also, selective peptide based inhibitors of cathepsin K have been developed See Bromme, D., et al., 1996, *Biochem J* 315:85-89; Thompson, S. K., et al., 1997, *Proc Natl Acad Sci USA* 94:14249-14254, which are hereby incorporated by reference in their entirety. Accordingly, inhibitors of Cathepsin K can reduce bone resorption. Such inhibitors would be useful in treating disorders involving bone resorption, such as osteoporosis.

SUMMARY OF THE INVENTION

The present invention relates to compounds that are capable of treating and preventing cathepsin dependent conditions or disease states in a mammal in need thereof. One embodiment of the present invention is illustrated by a compound of Formula I, and the pharmaceutically acceptable salts, stereoisomers and N-oxide derivatives thereof:

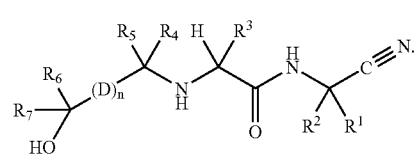

DETAILED DESCRIPTION OF THE INVENTION

The present invention relates to compounds of the following chemical formula:

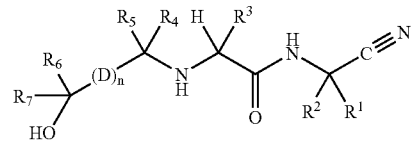

wherein $R^1$ and $R^2$ are taken together with the carbon atom to which they are attached to form a $C_{3-4}$ cycloalkyl which is optionally substituted with $C_{1-3}$ alkyl;

$R^3$ is $C_{1-6}$ alkyl which is substituted with one to four fluoro or one to four chloro;

$R^4$ is $C_{1-6}$ alkyl which is substituted with one to five halo;

$R^5$ is hydrogen or $C_{1-6}$ alkyl which is optionally substituted with one to five halo;

each D is independently aryl or heteroaryl;

$R^6$ is hydrogen or $C_{1-6}$ alkyl which is optionally substituted with one to two hydroxyl or two to six halo;

$R^7$ is $C_{1-6}$ alkyl which is optionally substituted with two to five halo;

n is two;

or a pharmaceutically acceptable salts, stereoisomers or N-oxide derivatives thereof.

In an embodiment of the invention, $R^1$ and $R^2$ are taken together with the carbon atom to which they are attached to form cyclopropyl.

In an embodiment of the invention, D is phenyl.

In an embodiment of the invention, $R^4$ is $CF_3$.

In an embodiment of the invention, $R^5$ is hydrogen.

In an embodiment of the invention, $R^7$ is $C_{1-3}$ alkyl substituted with two or three fluoro.

Reference to the preferred embodiments set forth above is meant to include all combinations of particular and preferred groups unless stated otherwise.

Specific embodiments of the present invention include, but are not limited to:

$N^1$-(1-cyanocyclopropyl)-$N^2$-(1-{4'-[2,2-difluoro-1-hydroxyethyl]biphenyl-4-yl}-2,2,2-trifluorothyl)-4-fluoro-L-leucinamide;

$N^1$-(1-cyanocyclopropyl)-4-fluoro-$N^2$-{2,2,2-trifluoro-1-[4'-(2,2,2-trifluoro-1-hydroxyethyl)biphenyl-4-yl]ethyl}-L-leucinamide;

$N^1$-(1-cyanocyclopropyl)-4-fluoro-$N^2$-(2,2,2-trifluoro-1-{4'-[3,3,3-trifluoro-1-hydroxy-1-methylpropyl]biphenyl-4-yl}ethyl)-L-leucinamide;

$N^1$-(1-cyanocyclopropyl)-4-fluoro-$N^2$-(2,2,2-trifluoro-1-{4'-[2,2,2-trifluoro-1-hydroxy-1-(trifluoromethyl)ethyl]biphenyl-4-yl}ethyl)-L-leucinamide;

$N^1$-(1-cyanocyclopropyl)-4-fluoro-$N^2$-{2,2,2-trifluoro-1-[4'-(2,2,2-trifluoro-1-hydroxy-1-methylethyl)biphenyl-4-yl]ethyl}-L-leucinamide;

$N^1$-(1-cyanocyclopropyl)-4-fluoro-$N^2$-(2,2,2-trifluoro-1-{4'-[1-hydroxy-1-(trifluoromethyl)propyl]biphenyl-4-yl}ethyl)-L-leucinamide;

$N^1$-(1-cyanocyclopropyl)-$N^2$-(1-{4'-[2,2-difluoro-1-hydroxy-1-methylethyl]biphenyl-4-yl}-2,2,2-trifluoroethyl)4-fluoro-L-leucinamide;

$N^1$-(1-cyanocyclopropyl)-$N^2$-(1-{4'-[2,2-difluoro-1-hydroxy-1-(hydroxymethyl)ethyl]biphenyl-4-yl}-2,2,2-trifluoroethyl)-4-fluoro-L-leucinamide;

$N^2$-[1-(4-bromophenyl)-2,2,2-trifluoroethyl]-$N^1$-(1-cyanocyclopropyl)-4-fluoro-L-leucinamide;

$N^1$-(1-cyanocyclopropyl)-$N^2$-((1S)-1-{4'-[(1R)-2,2-difluoro-1-hydroxyethyl]biphenyl-4-yl}-2,2,2-trifluoroethyl)-4-fluoro-L-leucinamide;

$N^1$-(1-cyanocyclopropyl)-$N^2$-((1S)-1-{4'-[(1S)-2,2-difluoro-1-hydroxyethyl]biphenyl-4-yl}-2,2,2-trifluoroethyl)-4-fluoro-L-leucinamide;

$N^1$-(1-cyanocyclopropyl)-4-fluoro-$N^2$-{(1S)-2,2,2-trifluoro-1-[4'-(2,2,2-trifluoro-1-hydroxyethyl)biphenyl-4-yl]ethyl}-L-leucinamide;

$N^1$-(1-cyanocyclopropyl)-4-fluoro-$N^2$-((1S)-2,2,2-trifluoro-1-{4'-[(1S)-3,3,3-triflouro-1-hydroxy-1-methylpropyl]biphenyl-4-yl}ethyl)-L-leucinamide;

$N^1$-(1-cyanocyclopropyl)-4-fluoro-$N^2$-((1S)-2,2,2-trifluoro-1-{4'-[(1R)-3,3,3-trifluoro-1-hydroxy-1-methylpropyl]biphenyl-4-yl}ethyl)-L-leucinamide;

$N^1$-(1-cyanocyclopropyl)-4-fluoro-$N^2$-{(1S)-2,2,2-trifluoro-1-[4'-(R)-(2,2,2-trifluoro-1-hydroxyethyl)biphenyl-4-yl]ethyl}-L-leucinamide;

$N^1$-(1-cyanocyclopropyl)-4-fluoro-$N^2$-((1S)-2,2,2-trifluoro-1-{4'-[2,2,2-trifluoro-1-hydroxy-1-(trifluoromethyl)ethyl]biphenyl-4-yl}ethyl)-L-leucinamide;

$N^1$-(1-cyanocyclopropyl)-4-fluoro-$N^2$-{(1S)-2,2,2-trifluoro-1-[4'-(2,2,2-trifluoro-1-hydroxy-1-methylethyl)biphenyl-4-yl]ethyl}-L-leucinamide;

of $N^1$-(1-cyanocyclopropyl)-4-fluoro-$N^2$-((1S)-2,2,2-trifluoro-1-{4'-[1-hydroxy-1-(trifluoromethyl)propyl]biphenyl-4-yl}ethyl)-L-leucinamide;

$N^1$-(1-cyanocyclopropyl)-$N^2$-((1S)-1-{4'-[(1R)-2,2-difluoro-1-hydroxy-1-methylethyl]biphenyl-4-yl}-2,2,2-trifluoroethyl)-4-fluoro-L-leucinamide;

$N^1$-(1-cyanocyclopropyl)-$N^2$-((1S)-1-{4'-[(1S)-2,2-difluoro-1-hydroxy-1-methylethyl]biphenyl-4-yl}-2,2,2-trifluoroethyl)-4-fluoro-L-leucinamide;

$N^1$-(1-cyanocyclopropyl)-$N^2$-((1S)-1-{4'-[(1S)-2,2-difluoro-1-hydroxy-1-(hydroxymethyl)ethyl]biphenyl-4-yl}-2,2,2-trifluoroethyl)-4-fluoro-L-leucinamide;

$N^1$-(1-cyanocyclopropyl)-$N^2$-((1S)-1-{4'-[(1R)-2,2-difluoro-1-hydroxy-1-(hydroxymethyl)ethyl]biphenyl-4-yl}-2,2,2-trifluoroethyl)-4-fluoro-L-leucinamide;

$N^2$-[(1S)-1-(4-bromophenyl)-2,2,2-trifluoroethyl]-$N^1$-(1-cyanocyclopropyl)-4-fluoro-L-leucinamide;

and the pharmaceutically acceptable salts, stereoisomers and N-oxide derivatives thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application.

Another embodiment of the present invention relates to an oral pharmaceutical composition comprising a compound of Formula I, or a pharmaceutically acceptable salt, stereoisomer or N-oxide derivative thereof, adapted for inhibiting bone resorption according to a continuous schedule having a dosage interval of once weekly, biweekly, twice monthly or once monthly.

These and other aspects of the invention will be apparent from the teachings contained herein.

Utilities

The compounds of the present invention are inhibitors of cathepsins and are therefore useful to treat or prevent cathepsin dependent diseases or conditions in mammals, preferably humans. Specifically, the compounds of the present invention are inhibitors of Cathepsin K and are therefore useful to treat or prevent Cathepsin K dependent diseases or conditions in mammals, preferably humans.

The compounds of the present invention have advantages over structurally similar compounds known in the art in that they have a marked improved pharmokinetic profile. Specifically, the compounds of the instant invention have excellent bioavailibilty, as exemplified, but not limited to, a dose of 10 milligrams per kilogram in male Sprague Dawley rats in 0.5-1% methocel. Additionally, the compounds of the instant invention provide greater drug systemic exposure than structurally similar compounds known in the art.

"Cathepsin dependent diseases or conditions" refers to pathologic conditions that depend on the activity of one or more cathepsins. "Cathepsin K dependent diseases or conditions" refers to pathologic conditions that depend on the activity of Cathepsin K. Diseases associated with Cathepsin K activities include osteoporosis, glucocorticoid induced osteoporosis, Paget's disease, abnormally disease, tooth loss, bone fractures, rheumatoid arthritis, osteoarthritis, periprosthetic osteolysis, osteogenesis imperfecta, atherosclerosis, obesity, glaucoma, chronic obstructive pulmonary disease and cancer including metastatic bone disease, hypercalcemia of malignancy, and multiple myeloma. In treating such conditions with the instantly claimed compounds, the required therapeutic amount will vary according to the specific disease and is readily ascertainable by those skilled in the art.

Although both treatment and prevention are contemplated by the scope of the invention, the treatment of these conditions is the preferred use.

An embodiment of the invention is a method of inhibiting cathepsin activity in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of treating or preventing cathepsin dependent conditions in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of inhibiting bone loss in a mammal in need thereof, comprising administering to the mammal a therapeutically effective amount of any of the compounds or any of the pharmaceutical compositions described above. Another embodiment of the invention is a method of reducing bone loss in a mammal in need thereof, comprising administering to the mammal a therapeutically effective amount of any of the compounds or any of the pharmaceutical compositions described above. A further embodiment of the invention is a method of treating abnormally increased bone turnover and bone fractures, in a mammal in need thereof, comprising administering to the mammal a therapeutically effective amount of any of the compounds or any of the pharmaceutical compositions described above. The utility of cathepsin K inhibitors in the inhibition of bone resorption is known in the literature, see Stroup, G. B., Lark, M. W., Veber, D F., Bhattacharrya, A., Blake, S., Dare, L. C., Erhard, K. F., Hoffman, S. J., James, I. E., Marquis, R. w., Ru, Y., Vasko-Moser, J. A., Smith, B. R., Tomaszek, T. and Gowen, M. Potent and selective inhibition of human cathepsin K leads to inhibition of bone resorption in vivo in a nonhuman primate. J. Bone Miner. Res., 16:1739-1746; 2001; and Votta, B. J., Levy, M. A., Badger, A., Dodds, R. A., James, I. E., Thompson, S., Bossard, M. J., Carr, T., Connor, J. R., Tomaszek, T. A., Szewczuk, L., Drake, F. H., Veber, D., and Gowen, M. Peptide aldehyde inhibitors of cathepsin K inhibit bone resorption both in vivo and in vitro. J. Bone Miner. Res. 12:1396-1406; 1997.

Another embodiment of the invention is a method of treating or preventing osteoporosis in a mammal in need thereof, comprising administering to the mammal a therapeutically effective amount of any of the compounds or any of the above pharmaceutical compositions described above. The utility of cathepsin K inhibitors in the treatment or prevention of osteoporosis, including glucocorticoid induced osteoporosis, is known in the literature, see Saftig, P., Hunziker, E., Wehmeyer, O., Jones, S., Boyde, A., Rommerskirch, W., Moritz, J. D., Schu, P., and Vonfigura, K. Impaired osteoclast bone resorption leads to osteopetrosis in cathepsin K-deficient mice. Proc. Natl. Acad. Sci. USA 95:13453-13458; 1998.

Another embodiment of the invention is a method of treating or preventing periodontal disease or tooth loss in a mammal in need thereof, comprising administering to the mammal a therapeutically effective amount of any of the compounds or any of the above pharmaceutical compositions described above. The utility of cathepsin K inhibitors in the treatment or prevention of periodontal disease or tooth loss has been discussed in the literature, see Sasaki, T., "Differentiation and functions of osteoclasts and osontoclasts in mineralized tissue resorption," Microsc Res Tech. 2003 August 15;61(6): 483-95.

Another embodiment of the invention is a method of treating or preventing rheumatoid arthritis or rheumatoid arthritic condition in a mammal in need thereof, comprising administering to the mammal a therapeutically effective amount of any of the compounds or any of the pharmaceutical compositions described above. It is known in the literature that progressive destruction of the periarticular bone is a major cause of joint dysfunction and disability in patients with rheumatoid arthritis (RA), see Goldring S R, "Pathogenesis of bone erosions in rheumatoid arthritis". Curr. Opin. Rheumatol. 2002; 14: 406-10. Analysis of joint tissues from patients with RA have provided evidence that cathepsin K positive osteoclasts are the cell types that mediate the focal bone resorption associated with rheumatoid synovial lesion, see Hou, W-S, Li, W, Keyszer, G, Weber, E, Levy, R, Klein, M J, Gravallese, E M, Goldring, S R, Bromme, D, "Comparison of Cathepsin K and S expression within the Rheumatoid and Osteoarthritic Synovium", Arthritis Rheumatism 2002; 46: 663-74. In addition, generalized bone loss is a major cause of morbidity associated with severe RA. The frequency of hip and spinal fractures is substantially increased in patients with chronic RA, see Gould A, Sambrook, P, Devlin J et al, "Osteoclastic activation is the principal mechanism leading to secondary osteoporosis in rheumatoid arthritis". J. Rheumatol. 1998; 25: 1282-9. The utility of cathepsin K inhibitors in the treatment or prevention of resorption in subarticular bone and of generalized bone loss represent a rational approach for pharmacological intervention on the progression of rheumatoid arthritis.

Another embodiment of the invention is a method of treating or preventing the progression of osteoarthritis in a mammal in need thereof, comprising administering to the mammal a therapeutically effective amount of any of the compounds or any of the pharmaceutical compositions described above. It is known in the literature that osteoarthritis (OA) is accompanied with well-defined changes in the joints, including erosion of the articular cartilage surface, peri-articular endochondral ossification/osteophytosis, and subchondral bony sclerosis and cyst formation, see Oettmeier R, Abendroth, K, "Osteoarthritis and bone: osteologic types of osteoarthritis of the hip", Skeletal Radiol. 1989; 18: 165-74. Recently, the potential contribution of subchondral bone sclerosis to the initiation and progression of OA have been suggested. Stiffened subchondral bone as the joint responding to repetitive impulsive loading, is less able to attenuate and distribute forces through the joint, subjecting it to greater mechanical stress across the articular cartilage surface. This in turn accelerates cartilage wear and fibrillate, see Radin, E L and Rose R M, "Role of subchondral bone in the initiation and progression of cartilage damage", Clin. Orthop. 1986; 213: 34-40. Inhibition of excessive subarticular bone resorption by an anti-resorptive agent such as a cathepsin K inhibitor, will lead to inhibition of subchondral bone turnover, thus may have a favorable impact on OA progression.

In addition to the above hypothesis, cathepsin K protein expression was recently identified in synovial fibroblasts, macrophage-like cells, and chondrocytes from synovium and articular cartilage specimens derived from OA patients, see Hou, W-S, Li, W, Keyszer, G, Weber, E, Levy, R, Klein, M J, Gravallese, E M, Goldring, S R, Bromme, D, "Comparison of Cathepsin K and S expression within the Rheumatoid and Osteoarthritic Synovium", Arthritis Rheumatism 2002; 46: 663-74; and Dodd, R A, Connor, J R, Drake, F H, Gowen, M, "Expression of Cathepsin K messenger RNA in giant cells and their precursors in human osteoarthritic synovial tissues".

Arthritis Rheumatism 1999; 42: 1588-93; and Konttinen, Y T, Mandelin, J, Li, T-F, Salo, J, Lassus, J et al. "Acidic cysteine endoproteinase cathepsin K in the degeneration of the superficial articular hyaline cartilage in osteoarthritis", Arthritis Rheumatism 2002; 46: 953-60. These recent studies thus implicated the role of cathepsin K in the destruction of collagen type II in the articular cartilage associated with the progression of osteoarthritis. The utility of cathepsin K inhibitors in the treatment or prevention of osteoarthritis as described in this invention thus comprise of two different mechanisms, one is on the inhibition of osteoclast-driven subchondral bone turnover, and two is on the direct inhibition of collagen type II degeneration in the synovium and cartilage of patients with OA.

Another embodiment of the invention is a method of treating periprosthetic osteolysis, in a mammal in need thereof, comprising administering to the mammal a therapeutically effective amount of any of the compounds or any of the pharmaceutical compositions described above. The use of cathepsin K inhibitors for the treatment of periprosthetic osteolysis is discussed in the literature, see, Mandelin, J., et al., "Interface tissue fibroblasts from loose total hip replacement prosthesis produce receptor activator of nuclear factor-kappaB ligand, osteoprotegerin and cathepsin K," J Rheumatol. 2005 April; 32(4):713-20.

Another embodiment of the invention is a method of treating bone disease, such as Paget's disease, osteogenesis imperfecta and bone lesions from multiple myeloma, in a mammal in need thereof, comprising administering to the mammal a therapeutically effective amount of any of the compounds or any of the pharmaceutical compositions described above. The use of cathepsin K inhibitors for the treatment of Paget's disease, osteogenesis imperfecta and bone lesions from multiple myeloma is discussed in the literature, see, Lipton, A., "New therapeutic agents for the treatment of bone diseases," Expert Opin Biol Ther. 2005 June;5(6):817-32.

Another embodiment of the invention is a method of treating cancer in a mammal in need thereof, comprising administering to the mammal a therapeutically effective amount of any of the compounds or any of the pharmaceutical compositions described above. It is known in the literature that cathepsin K is expressed in human breast carcinoma, prostate cancer and chordoma and has matrix degrading capabilities, see Littlewood-Evans A J, Bilbe G, Bowler W B, Farley D, Wlodarski B, Kokubo T, Inaoka T, Sloane J, Evans D B, Gallagher J A, "The osteoclast-associated protease cathepsin K is expressed in human breast carcinoma," Cancer Res 1997 December 1;57(23):5386-90. Brubaker K D, Vessella R L, True L D, Thomas R, Corey E, "Cathepsin K mRNA and protein expression in prostate cancer progression," J Bone Miner Res 2003 18, 222-30. Haeckel C, Krueger S, Kuester D, Ostertag H, Samii M, Buehling F, Broemme D, Czerniak B, Roessner A, "Expression of cathepsin K in chordoma," Hum Pathol 2000 July;31(7):834-40.

Another embodiment of the invention is a method of treating atherosclerosis in a mammal in need thereof, comprising administering to the mammal a therapeutically effective amount of any of the compounds or any of the pharmaceutical compositions described above. It is known in the literature that cathepsin K is expressed in human atheroma and has significant elastase activity, see Sukhova G K, Shi G P, Simon D I, Chapman H A, Libby P, "Expression of the elastolytic cathepsins S and K in human atheroma and regulation of their production in smooth muscle cells," J Clin Invest 1998 August 102, 576-83.

Another embodiment of the invention is a method of treating obesity in a mammal in need thereof, comprising administering to the mammal a therapeutically effective amount of any of the compounds or any of the pharmaceutical compositions described above. It is known in the literature that cathepsin K mRNA is increased in adipose tissue in several mouse models of obesity and also in adipose tissue of obese human males, see Chiellini C, Costa M, Novelli S E, Amri E Z, Benzi L, Bertacca A, Cohen P, Del Prato S, Friedman J M, Maffei M, "Identification of cathepsin K as a novel marker of adiposity in white adipose tissue," J Cell Physiol 2003, 195, 309-21.

Another embodiment of the invention is a method of treating glaucoma in a mammal in need thereof, comprising administering to the mammal a therapeutically effective amound of any of the compounds or any of the pharmaceutical compositions described above. Cathepsin K is highly expressed in the iris, cillary body and retinal pigment epithelium, and as such can be useful in the treatment of glaucoma, see Ortega, J., et al., "Gene Expression of Proteases and Protease Inhibitors in the Human Ciliary Epithelium and ODM-2 cells," Exp. Eye Res (1997) 65, 289-299; International Publication WO 2004/058238 (Alcon, Inc.).

Another embodiment of the invention is a method of treating chronic obstructive pulmonary disease in a mammal in need thereof, comprising administering to the mammal a therapeutically effective amount of any of the compounds or any of the pharmaceutical compositions described above. It is known in the literature that cathepsin K plays a role in lung fibrosis, see Buhling, F., et al., "Pivotal role of cathepsin K in lung fibrosis," Am J Pathol. 2004 June;164(6):2203-16.

Another embodiment of the invention is a method of treating parasitic infections in a mammal in need thereof, comprising administering to the mammal a therapeutically effective amount of any of the compounds or any of the pharmaceutical compositions described above. It is known in the literature that mammalian cathepsins are related to the papain-like cysteine proteases which play an important role in the life cycle of these parasites. Such parasites are involved in the diseases of malaria, American trypanosomiasis, African trypanosomiasis, leishmaniasis, giardiasis, trichomoniasis, amoebiasis, schistosomiasis, fascioliasis, paragonimiasis and intestinal roundworms, see Lecaille F, Kaleta J, Bromme D., Human and parasitic papain-like cysteine proteases: their role in physiology and pathology and recent developments in inhibitor design. Chem Rev 2002 102, 4459-88.

Another embodiment of the invention is a method of treating severe acute respiratory syndrome (SARS) in a mammal in need thereof, comprising administering to the mammal a therapeutically effective amount of any of the compounds or any of the pharmaceutical compositions described above.

Another embodiment of the invention is a method of treating metastatic bone disease in a mammal in need thereof, comprising administering to the mammal a therapeutically effective amount of any of the compounds or any of the pharmaceutical compositions described above. It is known in the literature that osteoclasts are responsible for bone resorption and that bone destruction and hypercalcemia induced by metastatic tumors are carried out by osteoclasts. Accordingly, the inhibition of osteoclasts can prevent bone destruction and bone metastasis, see Miyamoto, T. and Suda, T., "Differentiation and function of osteoclasts," Keio J Med 2003 March; 52(1):1-7.

Another embodiment of the invention is administering to a mammal a therapeutically effective amount of any of the compounds or any of the pharmaceutical compositions described above for the treatment of mammalian diseases associated with cathepsin S including Alzheimer's disease, atherosclerosis, chronic obstructive pulmonary disease, cancer and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immune responses, including, but not limited to, rejection of organ transplants or tissue grafts. It is known in the literature that cathepsin S activity is associated with the above disease states, see Munger J S, Haass C, Lemere C A, Shi G P, Wong W S, Teplow D B, Selkoe D J, Chapman H A, "Lysosomal processing of amyloid precursor protein to A beta peptides: a distinct role for cathepsin S," Biochem J 1995 311, 299-305. Sukhova G K, Zhang Y, Pan J H, Wada Y, Yamamoto T, Naito M, Kodama T, Tsimikas S, Witztum J L, Lu M L, Sakara Y, Chin M T, Libby P, Shi G P, "Deficiency of cathepsin S reduces atherosclerosis in LDL receptor-deficient mice," J Clin Invest 2003 111, 897-906. Zheng T, Zhu Z, Wang Z, Homer R J, Ma B, Riese R J Jr, Chapman H A Jr, Shapiro S D, Elias J A, "Inducible targeting of IL-13 to the adult lung causes matrix metalloproteinase- and cathepsin-dependent emphysema," J Clin Invest 2000 106,1081-93. Shi G P, Sukhova G K, Kuzuya M, Ye Q, Du J, Zhang Y, Pan J H, Lu M L, Cheng X W, Iguchi A, Perrey S, Lee A M, Chapman H A, Libby P, "Deficiency of the cysteine protease cathepsin S impairs microvessel growth," Circ Res 2003 92, 493-500. Nakagawa T Y, Brissette W H, Lira P D, Griffiths R J, Petrushova N, Stock J, McNeish J D, Eastman S E, Howard E D, Clarke S R, Rosloniec E F, Elliott E A, Rudensky A Y, "Impaired invariant chain degradation and antigen presentation and diminished collagen-induced arthritis in cathepsin S null mice," Immunity 1999 10,207-17.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

Further exemplifying the invention is the use of a cathepsin K inhibitor of the instant invention, or a pharmaceutically acceptable salt, stereoisomer or N-oxide derivative thereof, for the manufacture of a medicament, as an oral unit dose for treating a disorder selected from: osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, atherosclerosis, obesity, glaucoma, chronic obstructive pulmonary disease, metastatic bone disease, hypercalcemia of malignancy or multiple myeloma, in a mammal in need thereof according to a continuous schedule having a dosage interval of once weekly, biweekly, twice monthly or once monthly. Also exemplifying the invention is a method of treating a disorder selected from: osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, atherosclerosis, obesity, glaucoma, chronic obstructive pulmonary disease, metastatic bone disease, hypercalcemia of malignancy or multiple myeloma, by adminisitering a cathepsin K inhibitor of the instant invention to a mammal in need thereof according to a continuous schedule having a dosage interval of once weekly, biweekly, twice monthly or once monthly.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

In the case of tablets for oral use, carriers which are commonly used include lactose and corn starch, and lubricating agents, such as magnesium stearate, are commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; an estrogen receptor modulator; an androgen receptor modulator; an inhibitor of osteoclast proton ATPase; an inhibitor of HMG-CoA reductase; an integrin receptor antagonist; an Vitamin D; a synthetic Vitamin D analogue; anabolic agent, such as PTH; a Nonsteroidal anti-inflammatory drug; a selective cyclooxygenase-2 inhibitor; an inhibitor of interleukin-1 beta; a LOX/COX inhibitor; a RANKL inhibitor; and the pharmaceutically acceptable salts and mixtures thereof. A preferred combination is a compound of the present invention and an organic bisphosphonate. Another preferred combination is a compound of the present invention and an estrogen receptor modulator. Another preferred combination is a compound of the present invention and an androgen receptor modulator. Another preferred combination is a compound of the present invention and an osteoblast anabolic agent.

"Organic bisphosphonate" includes, but is not limited to, compounds of the chemical formula

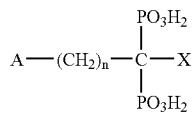

wherein n is an integer from 0 to 7 and wherein A and X are independently selected from the group consisting of H, OH, halogen, $NH_2$, SH, phenyl, $C_1$-$C_{30}$ alkyl, $C_3$-$C_{30}$ branched or cycloalkyl, bicyclic ring structure containing two or three N, $C_1$-$C_{30}$ substituted alkyl, $C_1$-$C_{10}$ alkyl substituted $NH_2$, $C_3$-$C_{10}$ branched or cycloalkyl substituted $NH_2$, $C_1$-$C_{10}$ dialkyl substituted $NH_2$, $C_1$-$C_{10}$ alkoxy, $C_1$-$C_{10}$ alkyl substituted thio, thiophenyl, halophenylthio, $C_1$-$C_{10}$ alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a $C_3$-$C_{10}$ ring.

In the foregoing chemical formula, the alkyl groups can be straight, branched, or cyclic, provided sufficient atoms are selected for the chemical formula. The $C_1$-$C_{30}$ substituted alkyl can include a wide variety of substituents, nonlimiting examples which include those selected from the group consisting of phenyl, pyridyl, furanyl, pyrrolidinyl, imidazonyl, $NH_2$, $C_1$-$C_{10}$ alkyl or dialkyl substituted $NH_2$, OH, SH, and $C_1$-$C_{10}$ alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-$C_1$-$C_{10}$-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronate, which is also known as alendronic acid, 4-amino-1-hydroxybutylidene-1,1-bisphosphonic acid, alendronate sodium or alendronate monosodium trihydrate, 4-amino-1-hydroxybutylidene-1,1-bisphosphonic acid monosodium trihydrate.

Alendronate is described in U.S. Pat. No. 4,922,007, to Kieczykowski et al., issued May 1, 1990; U.S. Pat No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yamanouchi (incadronate, formerly known as cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and J. Org. Chem 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

1-hydroxy-2-imidazo-(1,2-a)pyridin-3-yethylidene (minodronate).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

It is recognized that mixtures of two or more of the bisphosphonate actives can be utilized.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 μg/kg body weight and preferably about 10 to about 2000 μg/kg of body weight. For alendronate monosodium trihydrate, common human doses which are administered are generally in the range of about 2 mg/day to about 40 mg/day, preferably about 5 mg/day to about 40 mg/day. In the U.S. presently approved dosages for alendronate monosodium trihydrate are 5 mg/day for preventing osteoporosis, 10 mg/day for treating osteoporosis, and 40 mg/day for treating Paget's disease.

In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week.

"Selective estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

An "estrogen receptor beta modulator" is a compound that selectively agonizes or antagonizes estrogen receptor beta (ERβAgonizing ERβ increases transcription of the tryptophan hydroxylase gene (TPH, the key enzyme in serotonin synthesis) via an ERβ mediated event. Examples of estrogen receptor beta agonists can be found in PCT International publication WO 01/82923, which published on Nov. 08, 2001, and WO 02/41835, which published on May 20, 2002, both of which are hereby incorporated by reference in their entirety.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone antiresorptive agents," DDT, 4: 163-172 (1999)), which is hereby incorporated by reference in its entirety.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

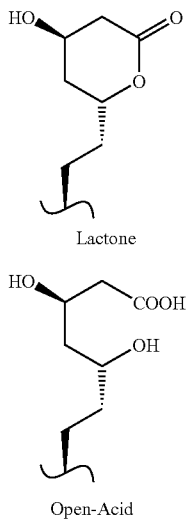

Lactone

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. H. N. Lode and coworkers in PNAS USA 96: 1591-1596 (1999) have observed synergistic effects between an antiangiogenic $\alpha v$ integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The $\alpha$ and $\beta$ integrin subunits interact non-covalently and bind extracellular matrix ligands in a divalent cation-dependent manner. The most abundant integrin on osteoclasts is $\alpha_v\beta_3$ ($>10^7$/osteoclast), which appears to play a rate-limiting role in cytoskeletal organization important for cell migration and polarization. The $\alpha_v\beta_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690-709 (1993). Studies have demonstrated the clinical benefits of parathyroid hormone in stimulating bone formation and thereby increasing bone mass and strength. Results were reported by R M Neer et al., in New Eng J Med 344 1434-1441 (2001).

In addition, parathyroid hormone-related protein fragments or analogues, such as PTHrP-(1-36) have demonstrated potent anticalciuric effects [see M. A. Syed et al., "Parathyroid hormone-related protein-(1-36) stimulates renal tubular calcium reabsorption in normal human volunteers: implications for the pathogenesis of humoral hypercalcemia of malignancy," JCEM 86: 1525-1531 (2001)] and may also have potential as anabolic agents for treating osteoporosis.

"Vitamin D" includes, but is not limited to, vitamin $D_3$ (cholecalciferol) and vitamin $D_2$ (ergocalciferol), which are naturally occurring, biologically inactive precursors of the hydroxylated biologically active metabolites of vitamin D: 1α-hydroxy vitamin D; 25-hydroxy vitamin D, and 1α,25-dihydroxy vitamin D. Vitamin $D_2$ and vitamin $D_3$ have the same biological efficacy in humans. When either vitamin $D_2$ or $D_3$ enters the circulation, it is hydroxylated by cytochrome $P_{450}$-vitamin D-25-hydroxylase to give 25-hydroxy vitamin D. The 25-hydroxy vitamin D metabolite is biologically inert and is further hydroxylated in the kidney by cytochrome P450-monooxygenase, 25 (OH) D-1α-hydroxylase to give 1,25-dihydroxy vitamin D. When serum calcium decreases, there is an increase in the production of parathyroid hormone (PTH), which regulates calcium homeostasis and increases plasma calcium levels by increasing the conversion of 25-hydroxy vitamin D to 1,25-dihydroxy vitamin D.

1,25-dihydroxy vitamin D is thought to be responsible for the effects of vitamin D on calcium and bone metabolism. The 1,25-dihydroxy metabolite is the active hormone required to maintain calcium absorption and skeletal integrity. Calcium homeostasis is maintained by 1,25 dihydroxy vitamin D by inducing monocytic stem cells to differentiate into osteoclasts and by maintaining calcium in the normal range, which results in bone mineralization by the deposition of calcium hydroxyapatite onto the bone surface, see Holick, M F, "Vitamin D photobiology, metabolism, and clinical applications," in *Endocrinology*, $3^{rd}$ ed., 990-1013 (1995), edited by DeGroot L, et al. However, elevated levels of $1\alpha25$-dihydroxy vitamin $D_3$ can result in an increase of calcium concentration in the blood and in the abnormal control of calcium concentration by bone metabolism, resulting in hypercalcemia. $1\alpha,25$-dihydroxy vitamin $D_3$ also indirectly regulates osteoclastic activity in bone metabolism and elevated levels may be expected to increase excessive bone resorption in osteoporosis.

In embodiments of the present invention, an appropriate amount of the vitamin D compound is chosen to provide adequate vitamin D nutrition during the dosing interval without interfering with the cathepsin K inhibitor's ability to obtain a bone resorption inhibiting effect. For oral compositions of the present invention comprising a cathepsin K inhibitor, and a vitamin D compound, an amount of the vitamin D compound comprises from about 100 IU to about 60,000 IU. Non-limiting examples of an oral amount of the vitamin D compound in embodiments of the present invention include, but are not limited to, dosages of 2,800, IU, 5,600 IU, 7,000 IU, 8,400 IU, 11,200 IU, 14,000 IU, 16,800 IU or 19,600 IU. Non-limiting examples of an oral amount of vitamin D for weekly dosing are 2,800, IU, 5,600 IU, 7,000 IU, 8,400 IU and 11,200 IU. Non-limiting examples of an oral amount of vitamin D for monthly dosing are 11,200 IU, 14,000 IU, 15,400 IU, 16,800 IU and 19,600 IU.

"Synthetic vitamin D analogues" includes non-naturally occurring compounds that act like vitamin D.

"Nonsteroidal anti-inflammatory drugs" or NSAIDs, inhibit the metabolism of arachidonic acid to proinflammatory prostaglandins via cyclooxygenase (COX)-1 and COX-2. Nonlimiting examples of NSAIDs include: aspirin, ibuprofen, naproxen, diclofenac, etodolac, fenoporfen, flubiprofen, indomethacin, ketoprofen, ketorolac, meloxicam, nabumetone, oxaprozin, piroxicam, sulindac, tolmetin, diflunisal, meclofenamate and phenylbutazone.

A "selective cyclooxygenase-2 inhibitor," or COX-2 inhibitor, refers to a type of nonsteroidal anti-inflammatory drug (NSAID), that inhibit the COX-2 coenzyme, which contributes to pain and inflammation in the body. Nonlimiting examples of COX-2 inhibitos include: celecoxib, etoricoxib, parecoxib, rofecoxib, valdecoxib and lumiracoxib.

An "inhibitor of interleukin-1 beta" or IL-1β, refers to in inhibitors of IL-1, which is a soluble factor produced by monocytes, macrophages, and other cells which activates T-lymphocytes and potentiates their response to mitogens or antigens. Nonlimiting examples of IL-1β inhibitors include diacerein and rhein.

A "LOX/COX inhibitor" refers to an inhibitor or all three of the major enzymes involved in arachidonic acid pathway— namely, 5-LOX, COX-1 and COX-2. A nonlimiting example of a LOX/COX inhibitor is licofelone.

A "RANKL inhibitor" refers to an inhibitor of receptor activator NF-kB ligand (RANKL), which has previously been called osteoclast differentiation factor (ODF), osteoprotegerin ligand (OPGL) and TNF-related activation induced cytokine (TRANCE). RANKL is a key stimulator of osteoclast formation and maturation. A nonlimiting example or a RANKL inhibitor is AMG-162.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Non-limiting examples of prodrugs envisioned by the current invention include esters that may be hydrolyzed to provide alcohols of the present invention; ketones that may be reduced in vivo to provide alcohols of the present invention. It is understood that in some cases, the reduction of a ketone may occur stereospecifically to provide predominantly a single diastereomeric alcohol. Further examples of suitable prodrugs, along with conventional procedures for the selection and preparation of such derivatives are described, for example, in "Design of Prodrugs," ed. H. Bundgaard, Elsevier, 1985, which is incorporated by reference herein in its entirety. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Metabolites of these compounds include active species produced upon introduction of compounds of this invention into the biological milieu.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

The term "bone resorption," as used herein, refers to the process by which osteoclasts degrade bone.

The terms "once weekly" and "once-weekly dosing," as used herein, means that a unit dosage, for example a unit dosage of a cathepsin K inhibitor, is administered once a week, i.e., once during a seven-day period, preferably on the same day of each week. In the once-weekly dosing regimen, the unit dosage is generally administered about every seven days. A non-limiting example of a once-weekly dosing regimen would entail the administration of a unit dosage of the cathepsin K inhibitor every Sunday. It is customarily recommended that a unit dosage for once-weekly administration is not administered on consecutive days, but the once-weekly dosing regimen can include a dosing regimen in which unit dosages are administered on two consecutive days falling within two different weekly periods.

By "biweekly" dosing is meant that a unit dosage of the cathepsin K inhibitor is administered once during a two week period, i.e. one time during a fourteen day period, preferably on the same day during each two week period. In the twice-weekly dosing regimen, each unit dosage is generally administered about every fourteen days. A nonlimiting example of a biweekly dosing regimen would entail the administration of a unit dosage of the cathepsin K inhibitor every other Sunday. It is preferred that the unit dosage is not administered on consecutive days, but the biweekly dosing regimen can include a dosing regimen in which the unit dosage is administered on two consecutive days within two different biweekly periods.

By "twice monthly" dosing is meant that a unit dosage of the cathepsin K inhibitor is administered twice, i.e. two times, during a monthly calendar period. With the twice monthly regimen, the doses are preferably given on the same two dates of each month. In the twice monthly dosing regimen, each unit dosage is generally administered about every fourteen to sixteen days. A nonlimiting example of a twice monthly dosing regimen would entail dosing on or about the first of the month and on or about the fifteenth, i.e. the midway point, of the month. It is preferred that the unit dosages are not administered on the same or consecutive days but the twice-monthly dosing regimen can include a dosing regimen in which the unit dosages are administered on two consecutive days within a monthly period, or different monthly periods. The twice monthly regimen is defined herein as being distinct from, and not encompassing, the biweekly dosing regimen because the two regimens have a different periodicity and result in the administration of different numbers of dosages over long periods of time. For example, over a one year period, a total of about twenty four dosages would be administered according to the twice monthly regimen (because there are twelve calendar months in a year), whereas a total of about twenty six dosages would be administered according to the biweekly dosing regimen (because there are about fifty-two weeks in a year).

The term "once monthly" is used in accordance with the generally accepted meaning as a measure of time amounting to approximately four weeks, approximately 30 days or $1/12$ of a calendar year.

The present invention also encompasses a pharmaceutical composition useful in the treatment of osteoporosis or other bone disorders, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for a cathepsin dependent condition. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 3.5, 5.0, 10.0, 15.0, 20.0, 25.0, 35.0, 40.0, 50.0, 80.0, 100, 200 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Also, the compounds of the present invention may be administered according to a continuous schedule having a dosage interval of once weekly, biweekly, twice monthly or once monthly. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The compounds of the present invention can be used in combination with other agents useful for treating cathepsin-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invention therefore encompasses the use of the instantly claimed compounds in combination with a second agent selected from: an organic bisphosphonate; an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; Vitamin D; a synthetic Vitamin D analogue; a Nonsteroidal anti-inflammatory drug; a selective cyclooxygenase-2 inhibitor; an inhibitor of interleukin-1 beta; a LOX/COX inhibitor; a RANKL inhibitor; and the pharmaceutically acceptable salts and mixtures thereof.

These and other aspects of the invention will be apparent from the teachings contained herein.

Definitions

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

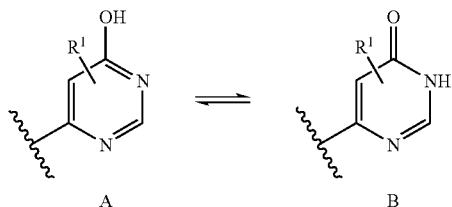

When any variable (e.g. $R^1$, $R^2$, $R^3$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having one to ten carbon atoms unless otherwise specified. For example, $C_1$-$C_{10}$, as in "$C_1$-$C_{10}$ alkyl" is defined to include groups having 1, 2, 3, 4, 5, 6, 7, 8, 9 or 10 carbons in a linear, branched, or cyclic arrangement. For example, "$C_1$-$C_{10}$ alkyl" specifically includes methyl, ethyl, propyl, butyl, pentyl, hexyl, heptyl, octyl, nonyl, decyl, and so on.

The term "cycloalkyl" or "carbocycle" shall mean cyclic rings of alkanes of three to eight total carbon atoms, unless otherwise indicated, or any number within this range (i.e., cyclopropyl, cyclobutyl, cyclopentyl, cyclohexyl, cycloheptyl or cyclooctyl).

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

As used herein, "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As appreciated by those of skill in the art, "halo" or "halogen" as used herein is intended to include chloro, fluoro, bromo and iodo. The term "keto" means carbonyl (C=O).

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," J. Pharm. Sci., 1977:66:1-19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

For purposes of this specification, the following abbreviations have the indicated meanings:
i-BuCOCl=isobutyl chloroformate
t-BuMe$_2$SiCl=tertio-butyldimethylchlorosilane
BuLi=butyl lithium
CH$_2$Cl$_2$=methylene chloride
CH$_3$CN=methyl cyanide
CrO$_3$=chromate
DAST=diethylaminosulfur trifluoride
DMF=N,N-dimethylformamide
DMSO=dimethylsulfoxide
DTT=dithiothreitol
EDTA=ethylenediaminetetraacetic acid
EtOH=ethanol
KOH=potassium hydroxide
HATU=2-(7-Aza-1H-benzotriazole-1-yl)-1,1,3,3-tetramethyluronium hexafluorophosphate
HCl=hydrochloric acid
H$_5$IO$_6$=periodic acid
MeMgBr=methyl magnesium bromide
MgSO$_4$=magnesium sulfate
Na$_2$CO$_3$=sodium carbonate
NaCl=sodium chloride
NH$_4$Cl=ammonium chloride
Na$_2$BH$_4$=sodium borohydride
PdCl$_2$(dppf)=[1,1'-bis(diphenylphosphino)ferrocene]dichloropalladium(II)
PG=protecting group
rt=room temperature
sat. aq.=saturated aqueous
SiO$_2$=silica
TBAF=tetrabutylammonium fluoride
THF=tetrahydrofuran
tlc=thin layer chromatography
(Ts)$_2$O=p-toluenesulfonic anhydride
Me=methyl
Et=ethyl The novel compounds of the present invention can be prepared according to the following general procedures using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

As describded in Example 12 and Scheme 1, starting with commercially available N-t-Boc-apartic acid beta benzyl ester, the free acid was activated via the mixed anhydride method (see, Chen, F. M. F.; Lee, Y; Steinauer, R., Benoiton, N. L., Can. J. Chem. 1987, 65, 613-618.) for reduction with sodium borohydride. The alcohol was converted to a leaving group and in situ cyclization to the carbamate occurred upon warming. The ester was treated with an excess of the Grignard reagent to produce the water-soluble tertiary alcohol. The latter was treated with DAST to obtain the fluorinated product. Hydrolysis of the cyclic carbamate and silylation of the resulting alcohol gave the primary amine. The imine was formed upon azeotropic removal of the volatiles. Monolithiation of 1,4-dibromobenzene afforded a nucleophile that nicely reacted with the imine to generate the secondary amine. The alcohol was deprotected and oxidized to yield the acid. Standard amide formation gave the versatile bromo intermediate.

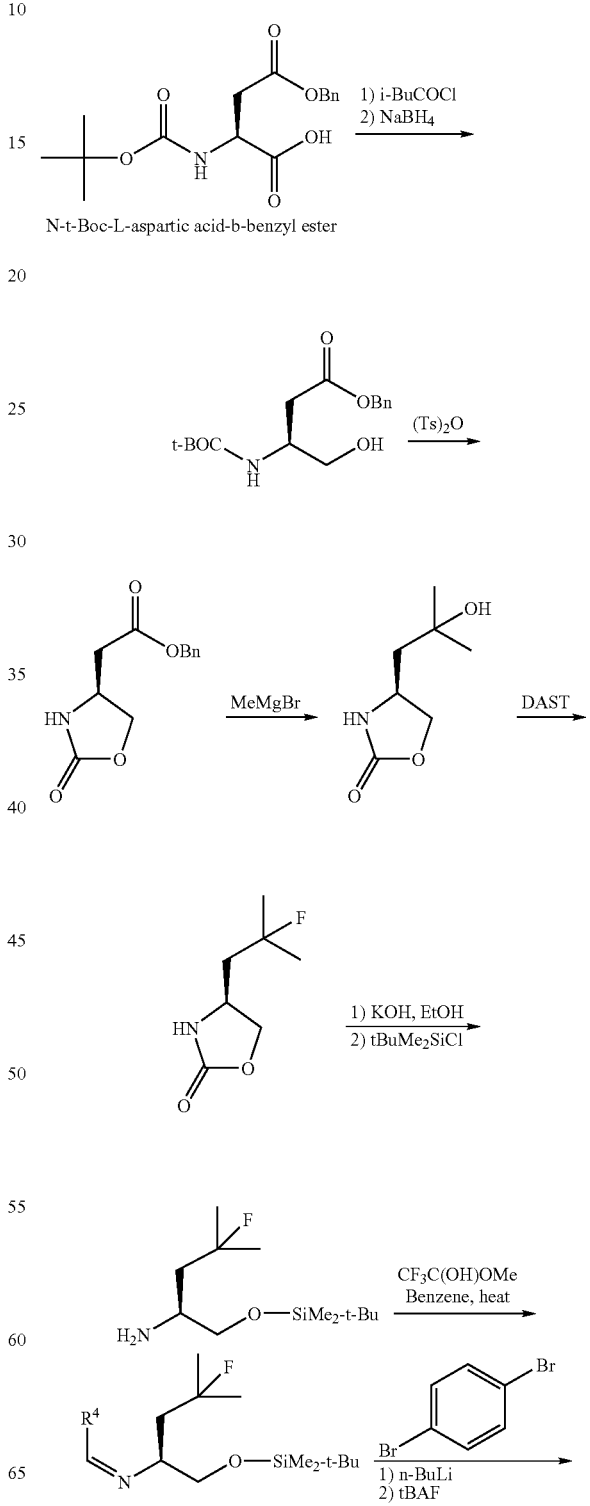

SCHEME 1

-continued

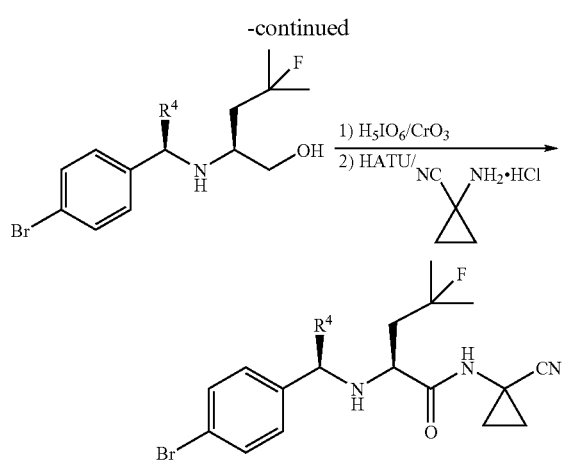

The bromo obtained in Scheme 1 can be converted to a boronate ester under palladium-mediated reaction conditions as shown in Scheme 2. In turn, the resulting boronate ester is easily converted to a biaryl product upon coupling with a bromide under palladium-mediated conditions.

SCHEME 2

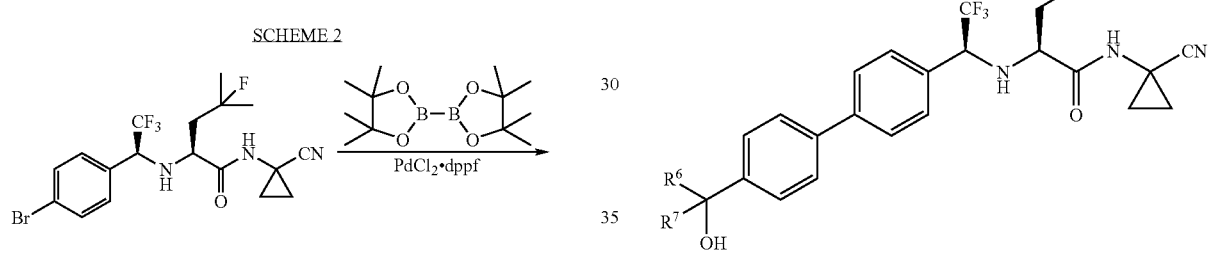

Alternatively, we show in Scheme 3 that an aryl bromide can be converted to a boronate ester under palladium cataly- sis. Under palladium-mediated reaction, this boronate ester can be coupled with the bromide describded in Scheme 1 to yield a biaryl compound.

SCHEME 3

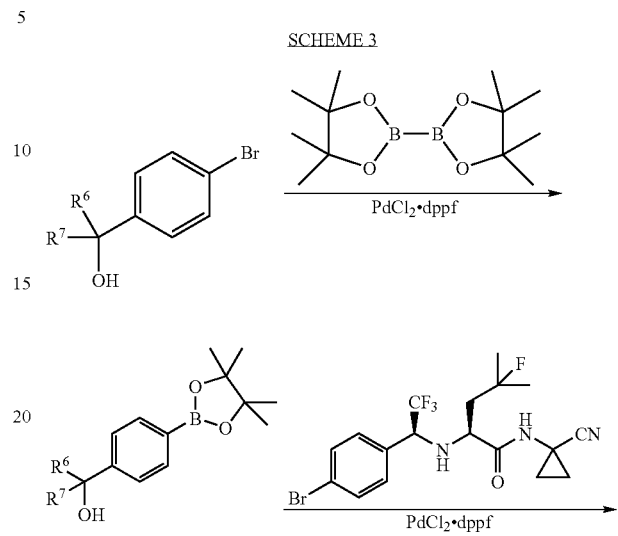

EXAMPLE 1

Synthesis of N$^1$-(1-cyanocyclopropyl)-N$^2$-((1S)-1-{4'-[(1R)-2,2-difluoro-1-hydroxyethyl]biphenyl-4-yl}-2,2,2-trifluoroethyl)-4-fluoro-L-leucinamide

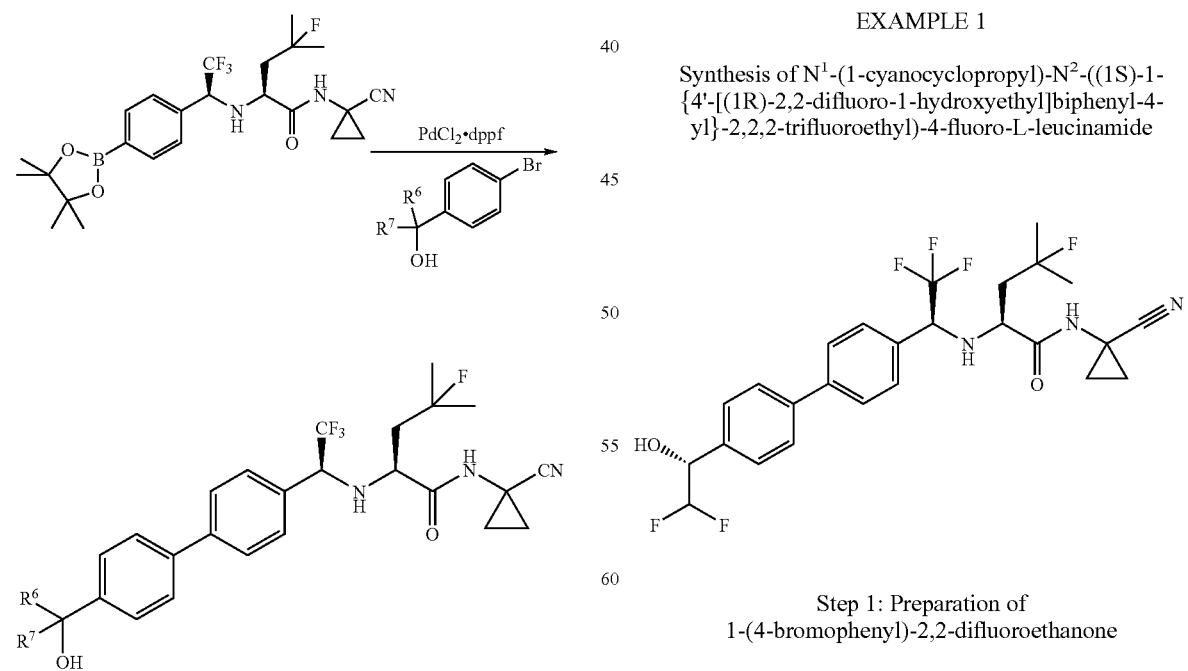

Step 1: Preparation of 1-(4-bromophenyl)-2,2-difluoroethanone

To a cold (−78° C.) stirred solution of 1,4-dibromobenzene (86.4 g, 366 mmol) in tetrahydrofuran (800 mL) was added n-butyllithium (228 mL, 1.6 M in hexanes, 366 mmol). This was stirred at −78° C. for 30 min and to this slurry was added ethyl difluoroacetate (50 g, 402 mmol) over 2 min. This was stirred at −78° C. for 1 h. The reaction was quenched with 1 N hydrochloric acid (250 mL) and let warm to room temperature. The media was diluted with methyl tert-butyl ether (250 mL) and the layers were separated. The organic was washed with brine (100 mL), dried (MgSO$_4$) and concentrated under reduced pressure. The residue was distilled under vacuum to obtain the difluoroketone as a white glassy solid.

Step 2: Preparation of (1R)-1-(4-bromophenyl)-2,2-difluoroethanol (Analogous to: Ramachandran, P. V. et al., Tet. Asym. 1994, Vol. 5. No. 6, pp. 1075-86.)

The ketone prepared in step 1 example 1 (2.35 g, 10 mmoles) and commercial R-Alpine Borane (3.1 g, 12 mmoles) were mixed together at room temperature and stirred for four days with some gas evolution. After four days, $^1$H NMR of an aliquot showed total consumption of the ketone. The reaction was cooled to 0° C. for the addition of acetaldehyde (168 uL, 3 mmoles). The bath was removed and stirring was continued at room temperature for 30 minutes. Diethyl ether (20 mL) was added followed by ethanolamine (725 uL, 12 mmoles). The mixture was stirred at room temperature for an hour. The precipitate was removed by filtration and washed with pentane. The filtrate was concentrated under reduced pressure and purified by flash chromatography (90% hexanes; 10% ethyl acetate to 70% hexanes; 30% ethyl acetate) to give the desired material as a colorless oil. The optical purity was not checked at this point.

Step 3: Preparation of N$^1$-(1-cyanocyclopropyl)-4-fluoro-N$^2$-{(1S)-2,2,2-trifluoro-1-[4-(4,4,5,5-tetramethyl-1,3,2-dioxaborolan-2-yl)phenyl]ethyl}-L-leucinamide N$^2$-[(1S)-1-(4-bromophenyl)-2,2,2-trifluoroethyl]-N$^1$-(1-cyanocyclopropyl)-4-fluoro-L-leucinamide from step 9 in example 12 (24 g, 53 mmol), bis(pinacolato)diboron (15.24 g, 60 mmoles) and potassium acetate (16.2 g, 165 mmoles) were stirred in dioxane (240 mL) and nitrogen was then bubbled through a pipette for 15 minutes. [1,1-Bis(diphenylphosphine)ferrocene] dichloropalladium(II), 1:1 complex with dichloromethane (PdCl$_2$dppf.CH$_2$Cl$_2$, 2.4 g, 3 mmoles) was added and the reaction mixture immersed in an oil bath at 80° C. for 105 minutes under a nitrogen atmosphere. $^1$H NMR of an aliquot showed total consumption of the bromide. The reaction was allowed to cool to room temperature and most of the solvent was removed under reduced pressure. The residue was dissolved in a minimum of dichloromethane and filtered on a pad of silica gel. Two fractions were collected and concentrated under reduced pressure to give solids. The least polar fraction was stirred at room temperature overnight in 90% hexanes; 10% diethylether mixture and the more polar fraction was stirred at 0° C. overnight in hexanes. Both gave pure material as off-white solids.

Step 4: Preparation of N$^1$-(1-cyanocyclopropyl)-N$^2$-((1S)-1-{4'-[(1R)-2,2-difluoro-1-hydroxyethyl]biphenyl-4-yl}-2,2,2-trifluoroethyl)-4-fluoro-L-leucinamide The boronate ester of step 3 of example 1 (20 g, 40 mmoles) and the aryl bromide of step 2 of example 1 (11.4 g, 48 mmoles) were dissolved in dimethylformamide (400 mL) followed by an aqueous solution of sodium bicarbonate (60 mL, 120 mmoles). Nitrogen was then bubbled through a pipette for 15 minutes. [1,1-Bis(diphenylphosphine)ferrocene]dichloropalladium(II), 1:1 complex with dichloromethane (PdCl$_2$dppf.CH$_2$Cl$_2$, 2.4 g, 3 mmoles) was added and the reaction mixture immersed in an oil bath at 80° C. for 16 hours under a nitrogen atmosphere. Most of the dimethylformamide was removed under the rotovap at low pressure (45° C., approx 1-5 mm Hg). The residue was dissolved in ethyl acetate (400 mL) and filtered onto a pad of Celite. The filtrate was concentrated under reduced pressure. The residue was taken-up in approx 10 mL of dichloromethane and separated by flash chromatography. The most pure fractions were swished in hexanes (100 mL) at 0° C. overnight three times and flashed again (90% hexanes; 10% ethyl acetate to 45 hexanes; 55% ethyl acetate). After evaporation of the volatiles under reduced pressure, the solid was stirred in hexanes for 2 days. The product still contained 4% of pinacol so the batch was divided in two. Fraction A was dissolved in a minimum of isopropyl alcohol with gentle warming. Hexanes were added until the solution was a bit cloudy and let cool down. White crystals appeared and the reaction was further cooled to 0° C. for 15 minutes. The solids were collected by filtration to obtain the product not contaminated with pinacol. Fraction B was stirred in 20% diethyl ether; 1% ethyl acetate; 79% hexanes (100 mL) for 3 hours at room temperature. The solids were collected by filtration which was contaminated with only approximately 1% pinacol by $^1$H NMR. The enantiomeric excess was verified chiral AD-RH using 32% acetonitrile; 68% water; 0.1% formic acid; isocratic (24 min for enantiomer and 27 minutes for desired molecule). (MH)$^+$ ESI=528.0.

EXAMPLE 2

Synthesis of N$^1$-(1-cyanocyclopropyl)-N$^2$-((1S)-1-{4'-[(1S)-2,2-difluoro-1-hydroxyethyl]biphenyl-4-}-2,2,2-trifluoroethyl)-4-fluoro-L-leucinamide

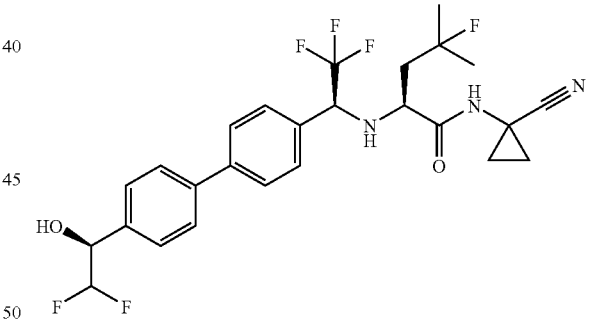

Step 1: Preparation of (1S)-1-(4-bromophenyl)-2,2-difluoroethanol

The ketone prepared in step 1 of example 1 (2.35 g, 10 mmoles) and commercial S-Alpine Borane (3.1 g, 12 mmoles) were mixed together at room temperature and stirred for four days with some gas evolution. After four days, $^1$H NMR of an aliquot showed the presence of starting material. More S-Alpine Borane (1 mL) was added and stirring continued for 2 additional days. $^1$H NMR of an aliquot showed total consumption of the ketone. The reaction was cooled to 0° C. for the addition of acetaldehyde (393 uL, 7 mmoles). The bath was removed and stirring was continued at room temperature for 30 minutes. Diethyl ether (20 mL) was added followed by ethanolamine (966 uL, 16 mmoles). The mixture was stirred at room temperature for an hour. The precipitate was removed by filtration and washed with pentane. The filtrate was concentrated under reduced pressure and purified by flash chromatography (90% hexanes; 10% ethyl acetate to 70% hexanes; 30% ethyl acetate) to give the desired material as a colorless oil.

Step 2: Preparation of $N^1$-(1-cyanocyclopropyl)-$N^2$-((1S)-1-{4'-[(1S)-2,2-difluoro-1-hydroxyethyl]biphenyl-4-yl}-2,2,2-trifluoroethyl)-4-fluoro-L-leucinamide The boronate ester of step 3 in example 1 (200 mg, 0.40 mmoles) and the aryl bromide of step 1 in example 2 (114 mg, 0.48 mmoles) were treated as in step 4 of example 1 to afford a white solid. (MH)$^+$ ESI=528.0

EXAMPLE 3

Synthesis of $N^1$-(1-cyanocyclopropyl)-4-fluoro-$N^2$-{(1S)-2,2,2-trifluoro-1-[4'-(2,2,2-trifluoro-1-hydroxyethyl)biphenyl-4-yl]ethyl}-L-leucinamide

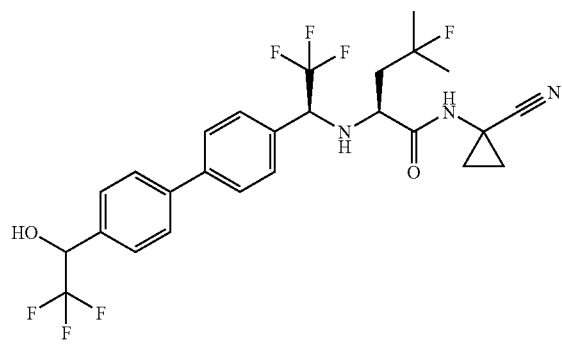

Step 1: Preparation of 1-(4-bromophenyl)-2,2,2-trifluoroethanol

To a room temperature solution of commercial 4'-bromo-2,2,2-trifluoroacetophenone (100 mg) in 1.9 mL of methanol was added sodium borohydride (15 mg). The mixture was stirred at room temperature overnight. Water was added, extracted with methyl t-butyl ether (3×20 mL) washed with water and brine. It was dried with magnesium sulfate and the solvent removed under reduced pressure to yield the title compound and it was used as such for the next step.
$^1$H NMR of title compound (CDCl$_3$) δ (ppm): 7.55(2H, d), 7.35(2H, d), 4.92-5.05(1H, m), 3.20(1H, s).

Step 2: Preparation of $N^1$-(1-cyanocyclopropyl)-4-fluoro-$N^2$-{(1S)-2,2,2-trifluoro-1-[4'-(2,2,2-trifluoro-1-hydroxyethyl)biphenyl-4-yl]ethyl}-L-leucinamide A stream of nitrogen was passed through a solution of DMF (4 mL), $N^1$-(1-cyanocyclopropyl)-4-fluoro-$N^2$-{(1S)-2,2,2-trifluoro-1-[4-(4,4,5,5-tetramethyl-1,3,2-dioxaborolan-2-yl)phenyl]ethyl}-L-leucinamide described in step 3 of example 1 (150 mg), 1-(4-bromophenyl)-2,2,2-trifluoroethanol from step 1 in example 3 (92 mg) and 2 M Na$_2$CO$_3$ (750 µL) for 15 minutes followed by the addition of [1,1'-bis (diphenylphosphino)-ferrocene]dichloropalladium(II), complex (1:1) with dichloromethane (12 mg). The mixture was warmed to 80° C. for 3 hours under nitrogen. The mixture was cooled to room temperature, poured into ice (20 g) and saturated aqueous sodium bicarbonate (20 mL) and extracted with 50% ethyl acetate in diethyl ether (3×50 mL). The combined extracts were washed with brine and dried with magnesium sulfate. Removal of the solvent left a residue that was purified by chromatography on SiO$_2$ using ethyl acetate and hexanes (20 to 50%) as eluent, followed by trituration using diethyl ether and hexanes to yield the title compound.
$^1$H NMR (CD$_3$COCD$_3$) δ (ppm): 8.18(1H, s), 7.60-7.70 (4H, m), 7.50-7.55(1H, m), 7.33(1H, d), 7.28(1H, d), 6.40 (1H, bs), 4.38-4.48(1H, m), 3.56 (1H, t), 2.67-2.69 (1H, m), 1.92-2.01 (2H, m), 1.45-1.46(10H, m), 1.05-1.11(3H, m), 0.92-0.99(1H, m), 0.56-0.60(2H, m), 0.36-0.38(2H, m).

EXAMPLE 4

Synthesis of $N^1$-(1-cyanocyclopropyl)-4-fluoro-$N^2$-((1S)-2,2,2-trifluoro-1-{4'-[(1S)-3,3,3-trifluoro-1-hydroxy-1-methylpropyl]biphenyl-4-yl}ethyl)-L-leucinamide and $N^1$-(1-cyanocyclopropyl)-4-fluoro-$N^2$-((1S)-2,2,2-trifluoro-1-{4'-[(1R)-3,3,3-trifluoro-1-hydroxy-1-methylpropyl]biphenyl-4-yl}ethyl)-L-leucinamide

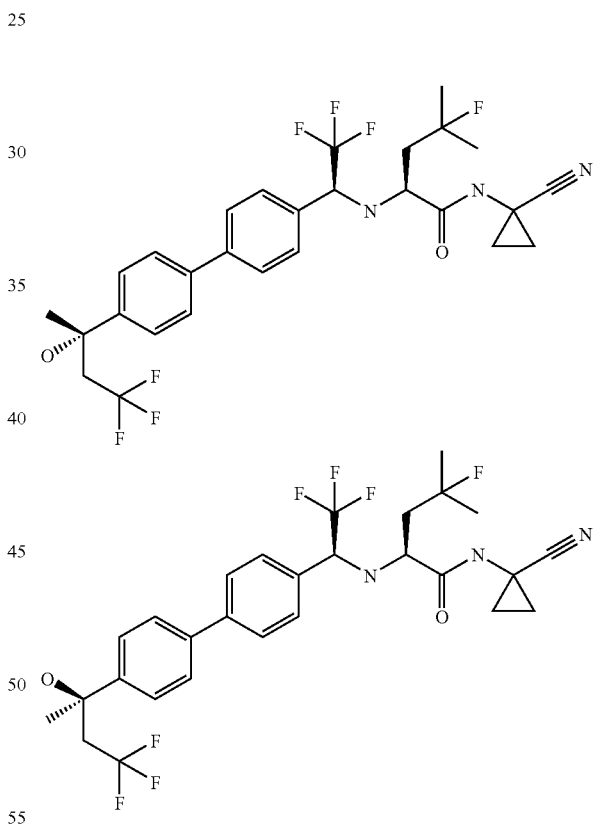

Step 1: Preparation of 2-(4-Bromophenyl)-4,4,4-trifluorobutan-2-ol

To a solution of 1,4-dibromobenzene (2.5 g, 10.6 mmol) in THF (50 mL) at −78° C. was added n-BuLi (6.5 mL, 10.4 mmol; 1.6 M in hexanes) and the mixture was stirred at −78° C. for 15 min. 4,4,4-Trifluoro-2-butanone (1.3 g, 10.3 mmol) was then added. After further stirring for 15 min., the mixture was quenched with aqueous NH$_4$Cl and extracted with Ethyl acetate. Purification by combi-flash chromatography (40 g column; eluted with hexanes—Ethyl acetate (10% -20%) in 20 min.; flow rate: 35 mL/min and collected 18 mL/fraction) yielded the title compound as a light brown liquid.

$^1$H NMR (CD$_3$COCD$_3$) δ (ppm): 7.5 (4H, m), 4.64 (1H, s), 1.64 (3H, s).

Step 2: Preparation of N$^1$-(1-cyanocyclopropyl)-4-fluoro-N$^2$-((1S)-2,2,2-trifluoro-1-{4'-[(1S)-3,3,3-trifluoro-1-hydroxy-1-methylpropyl]biphenyl-4-yl}ethyl)-L-leucinamide and N$^1$-(1-cyanocyclopropyl)-4-fluoro-N$^2$-((1S)-2,2,2-trifluoro-1-{4'-[(1R)-3,3,3-trifluoro-1-hydroxy-1-methylpropyl]biphenyl-4-yl}ethyl)-L-leucinamide A stream of nitrogen was passed through a solution of DMF (5 mL), N$^1$-(1-cyanocyclopropyl)-4-fluoro-N$^2$-{(1S)-2,2,2-trifluoro-1-[4-(4,4,5,5-tetramethyl-1,3,2-dioxaborolan-2-yl)phenyl]ethyl}-L-leucinamide described in step 3 of example 1 (150 mg), 2-(4-bromophenyl)4,4,4-trifluorobutan-2-ol from step 1 in example 4 (100 mg) and 2 M Na$_2$CO$_3$ (360 μL) for 15 minutes followed by the addition of [1,1'-bis(diphenylphosphino)-ferrocene]dichloropalladium(II), complex (1:1) with dichloromethane (5 mg). The mixture was warmed to 80° C. for 3 hours under nitrogen. The mixture was cooled to room temperature, poured into ice (20 g) and saturated aqueous sodium bicarbonate (20 mL) and extracted with 50% ethyl acetate in diethyl ether (3×50 mL). The combined extracts were washed with brine and dried with magnesium sulfate. Removal of the solvent left a residue that was purified by chromatography on silica gel using automatized gradiant pump system CombiFlash (Ethyl acetate/Hexane, 20:80 to 50:50 for 25 minutes) followed by trituration using diethyl ether and hexanes to yield the mixture of two diastereomers.

For separation, a 200 μL solution of the mixture of the two diastereomers (concentration at 50 μg/μL in 33% of 2-propanol and 67% hexanes) of N$^1$-(1-cyanocyclopropyl)-4-fluoro-N$^2$-{(1S)-2,2,2-trifluoro-1-[4'-(3,3,3-trifluoro-1-hydroxy-1-methylpropyl)biphenyl-4-yl]ethyl}-L-leucinamide was injected on Chiralcel OD, 250×20 mm (OD00C-CK004) using 33% of 2-propanol in hexanes as solvents, the flow at 6 mL/min and the detection at 260 nm. After several injections, N$^1$-(1-cyanocyclopropyl)-N$^2$-((1S)-1-{4'-[(1R)-2,2-difluoro-1-hydroxy-1-methylethyl]biphenyl-4-yl}-2,2,2-trifluoroethyl)-4-fluoro-L-leucinamide was isolated from the first eluting fractions and N$^1$-(1-cyanocyclopropyl)-N$^2$-((1S)-1-{4'-[(1S)-2,2-difluoro-1-hydroxy-1-methylethyl]biphenyl-4-yl}-2,2,2-trifluoroethyl)-4-fluoro-L-leucinamide was isolated from the second eluting fractions.

First eluting diastereomer: 1H NMR (CD$_3$COCD$_3$) δ (ppm): 8.19 (1H, s), 7.74-7.68 (6H, m), 7.57 (2H, d), 4.60 (1H, s), 4.42-4.36 (1H, m), 3.57-3.53 (1H, m), 2.78-2.88 (2H, m), 1.94-2.00 (2H, m), 1.73 (3H, s), 1.49-1.31 (8H, m), 1.07-1.13 (1H, m), 1.00-0.90 (1H, m), NH of trifluoroethylamine was not observed. (MH)$^+$ APCI=573.9. Stereochemistry is tentative.

Second eluting diastereomer: 1H NMR (CD$_3$COCD$_3$) δ (ppm): 8.19 (1H, s), 7.74-7.68 (6H, m), 7.57 (2H, d), 4.60 (1H, s), 4.42-4.36 (1H, m), 3.57-3.53 (1H, m), 2.78-2.88 (2H, m), 1.94-2.00 (2H, m), 1.73 (3H, s), 1.49-1.31 (8H, m), 1.07-1.13 (1H, m), 1.00-0.90 (1H, m), NH of trifluoroethylamine was not observed. (MH)$^+$ APCI=574.0. Stereochemistry is tentative.

EXAMPLE 5

Synthesis of N$^1$-(1-cyanocyclopropyl)-4-fluoro-N$^2$-{(1S)-2,2,2-trifluoro-1-[4'-(R)-(2,2,2-trifluoro-1-hydroxyethyl)biphenyl-4-yl]ethyl}-L-leucinamide

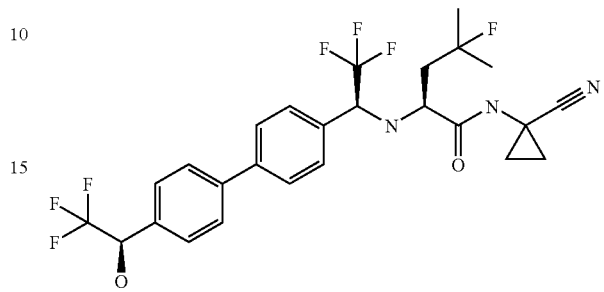

Step 1: Preparation of (R)-2,2,2-trifluoro-1-[4-(4,4,5,5-tetramethyl-1,3,2-dioxaborolan-2-yl)phenyl]ethanol A suspension of (R)-1-(4-bromophenyl)-2,2,2-trifluoroethanol (2.26 g, 8.86 mmol), bis(pinacolato)diboron (2.9 g, 11 mmol) and potassium acetate (3 g, 30 mmol) in DMF (80 mL) was bubbled with nitrogen for 15 minutes [1,1-Bis(diphenylphosphine)ferrocene]dichloropalladium(II), 1:1 complex with dichloromethane (362 mg, 0.44 mmol) was added and bubbled again with nitrogen for 10 minutes. The reaction mixture was stirred at 85° C. for 2 h, poured on ice and water and extracted with Ethyl acetate (2×80 mL). The combined organic layers were washed with a saturated NaCl solution, dried (MgSO4) and concentrated under vacuum. The residue was purified by chromatography on silica gel (Ethyl acetate/Hexane, 5:95 to 20:80 for 25 minutes then 20:80 for 5 minutes) to afford the title product.

$^1$H NMR (CD$_3$COCD$_3$) δ (ppm): 7.8(2H, d), 7.55(2H, d), 5.9(1H, OH), 5.2-5.3(1H, m), 1.3(12H, s).

Step 2: Preparation of N$^1$-(1cyanocyclopropyl)-4-fluoro-N$^2$-{(1S)-2,2,2-trifluoro-1-[4'-(R)-(2,2,2-trifluoro-1-hydroxyethyl)biphenyl-4-yl]ethyl}-L-leucinamide The boronate ester from step 1 in example 5 (250 mg, 0.83 mmol) and N$^2$-[(1S)-1-(4-bromophenyl)-2,2,2-trifluoroethyl]-N$^1$-(1-cyanocyclopropyl)-4-fluoro-L-leucinamide (374 mg, 0.83 mmol) from step 9 in example 12 were coupled as in step 4 of example 1 to provide the title compound as off-white powder.

$^1$H NMR (CD$_3$COCD$_3$) δ (ppm): 8.1-8.2(1H, bs), 7.75-7.8 (4H, m), 7.7 (2H, m), 7.6(2H, m), 5.9(1H, m), 5.25-5.35(1H, m), 4.35(1H, m), 3.5-3.6(1H, m), 1.9-2.1(2.H, m), 1.2-1.6 (8H, m), 0.9-1.1(2H, m); NH not observed. (MH)$^+$ ESI=545.8.

EXAMPLE 6

Synthesis of N¹-(1-cyanocyclopropyl)-4-fluoro-N²-((1S)-2,2,2-trifluoro-1-{4'-[2,2,2-trifluoro-1-hydroxy-1-(trifluoromethyl)ethyl]biphenyl-4-yl}ethyl)-L-leucinamide

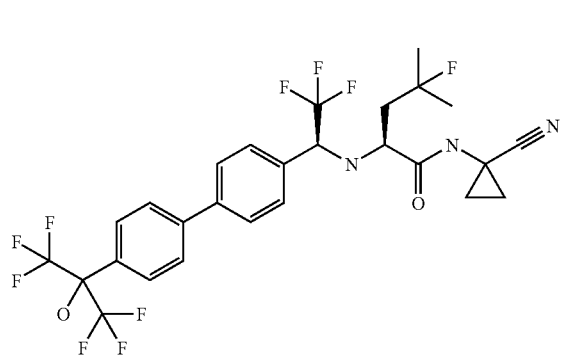

Step 1: Preparation of 2-(4-bromophenyl)-,1,1,1,3,3,3-hexafluoropropan-2-ol

To a −78° C. solution of dibromobenzene (4.7 g) in tetrahydrofuran (100 mL) was added n-butyllithium (8 mL; 2.5 M in hexanes) and the mixture was stirred for 15 minutes. A gentle stream of hexafluoroacetone was then passed through the suspension for about 15 minutes. The mixture was then allowed to react for 1 hour. It was poured into ice and dilute ammonium chloride and extracted with ethyl acetate. The organic layer was dried with magnesium sulfate and the solvent was removed under reduced pressure using minimal heat. The residue was passed on a short bed of SiO2 using 10% ethyl acetate/90% hexanes as the eluent to yield the tertiary alcohol.

¹H NMR (CD₃COCD₃) δ (ppm): 7.75-7.8(4H, s), 7.65(1H, OH).

Step 2: Preparation of N¹-(1-cyanocyclopropyl)-4-fluoro-N²-((1S)-2,2,2-trifluoro-1-{4'-[2,2,2-trifluoro-1-hydroxy-1-(trifluoromethyl)ethyl]biphenyl-4-yl}ethyl)-L-leucinamide N¹-(1-cyanocyclopropyl)-4-fluoro-N²-{(1S)-2,2,2-trifluoro-1-[4-(4,4,5,5-tetramethyl-1,3,2-dioxaborolan-2-yl)phenyl]ethyl}-L-leucinamide described in step 3 of example 1. (220 mg, 0.44 mmoles) and the bromide from step 1 in example 6 (323 mg, 1 mmol) were coupled as in step 4 of example 1 to provide the title compound as a foam.

¹H NMR (CD₃COCD₃) δ (ppm): 8.2(1H, bs), 7.85-7.95 (4H, m), 7.75-7.8(2H, d), 7.6(2H, d), 7.55(1H, OH), 4.4(1H, m), 3.55(1H, m), 2.8-2.9(1H, m), 1.9-2.1(2H, m), 1.4-1.5(6H, m), 1.3-1.4(2H, m), 1.1(1H, m), 0.95(1H, m). (MH)⁺ ESI=614.1.

EXAMPLE 7

Synthesis of N¹-(1-cyanocyclopropyl)-4-fluoro-N²-{(1S)-2,2,2-trifluoro-1-[4'-(2,2,2-trifluoro-1-hydroxy-1-methylethyl)biphenyl-4-yl]ethyl}-L-leucinamide

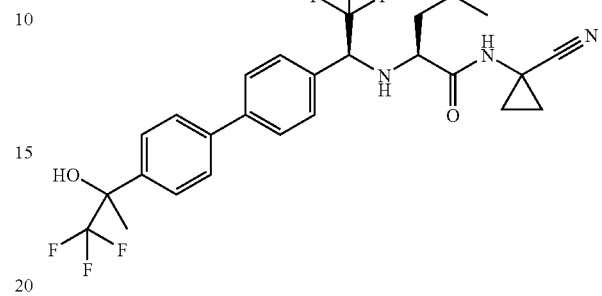

Step 1: Preparation of 2-(4-bromophenyl)-1,1,1-trifluoropropan-2-ol

Commercial 1-(4-bromophenyl)-2,2,2-trifluoroethanone (1 g, 4 mmoles) in diethyl ether (8 mL) was cooled to −78° C. for the addition of commercial methylmagnesium bromide (2.65 mL, 7.9 mmoles, 3 M in diethyl ether). The cloudy reaction media was allowed to reach room temperature and stirred overnight. The reaction mixture was transferred to a separatory funnel containing 1.2 M hydrochloric acid (20 mL). This aqueous layer was extracted 3 times with ethyl acetate (30 mL). The combined organic layers were washed with brine, dried over magnesium sulphate and concentrated under reduced pressure. The clear oil was pure enough to be used without further purification.

Step 2: Preparation of N¹-(1-cyanocyclopropyl)-4-fluoro-N²-{(1S)-2,2,2-trifluoro-1-[4'-(2,2,2-trifluoro-1-hydroxy-1-methylethyl)biphenyl-4-yl]ethyl}-L-leucinamide The boronate ester of step 3 in example 1 (250 mg) and the bromide from step 1 in example 7 (150 mg) were coupled as in step 4 of example 1 to provide the title compound as a white powder.

(MH)⁺ ESI=560

EXAMPLE 8

Synthesis of N¹-(1-cyanocyclopropyl)-4-fluoro-N²-((1S)-2,2,2-trifluoro-1-{4'-[1-hydroxy-1-(trifluoromethyl)propyl]biphenyl-4-yl}ethyl)-L-leucinamide

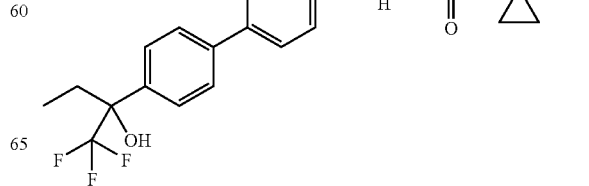

Step 1: Preparation of 2-(4-Bromophenyl)-1,1,1-trifluorobutan-2-ol

To a solution of 1,4-dibromobenzene (2.5 g, 10.6 mmol) in THF (50 mL) at −78° C. was added n-BuLi (6.5 mL, 10 mmol; 1.6 M in hexanes) and the mixture was stirred at −78° C. for 15 min. 1,1,1-Trifluoro-2-butanone (1.3 g, 10 mmol) was then added. After further stirring for 15 min., the mixture was quenched with aqueous NH$_4$Cl and extracted with Ethyl acetate. Purification by combi-flash chromatography (40 g column; eluted with hexanes—Ethyl acetate (10% -20%) in 20 min.; flow rate: 35 mL/min and collected 18 mL/fraction) to yield the title compound as a colorless liquid.

$^1$H NMR (CD3COCD3) δ (ppm): 7.58 (m, 5H), 5.52 (s, 1H), 2.28 (m, 1H), 2.10 (m, 1H).

Step 2: Preparation of N$^1$-(1-cyanocyclopropyl)-4-fluoro-N$^2$-((1S)-2,2,2-trifluoro-1-{4'-[1-hydroxy-1-(trifluoromethyl)propyl]biphenyl-4-yl}ethyl)-L-leucinamide The boronate ester of step 3 in example 1 (150 mg) and the bromide from step 1 in example 8 (100 mg) were coupled as in step 4 of example 1 to provide the title compound as a white powder.

(MH)$^+$ ESI=574

EXAMPLE 9

Synthesis of N$^1$-(1-cyanocyclopropyl)-N$^2$-((1S)-1-{4'-[(1R)-2,2-difluoro-1-hydroxy-1-methylethyl]biphenyl-4-yl}-2,2,2-trifluoroethyl)-4-fluoro-L-leucinamide and N$^1$-(1-cyanocyclopropyl)-N$^2$-((1S)-1-{4'-[(1S)-2,2-difluoro-1-hydroxy-1-methylethyl]biphenyl-4-yl}-2,2,2-trifluoroethyl)-4-fluoro-L-leucinamide

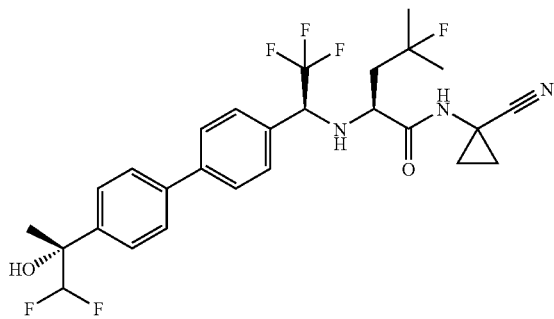

and

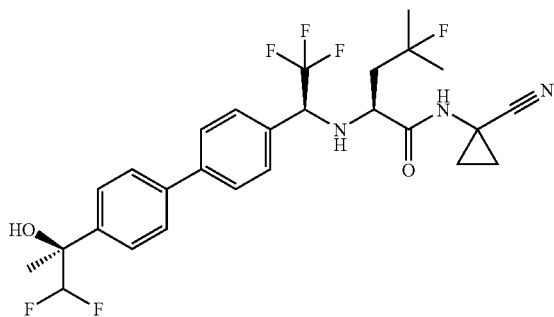

Step 1: Preparation of 2-(4-Bromophenyl)-1,1-difluoropropan-2-ol

To a solution of 1-(4-bromophenyl)-2,2-difluoroethanone (2.5 g, 10.6 mmol) in THF (60 mL) was added methylmagnesium chloride (10 mL, 30 mmol; 3 M in THF) at 0° C. over ~10 min and the mixture was stirred at 0° C. for 1 h. A mini-worked up showed starting material remained and more methylmagnesium chloride (5 mL, 15 mmol, 3 M in THF) was added. After further stirred for 15 min., the mixture was quenched with H$_2$O, carefully acidified with 1 M HCl (100 mL) and extracted with Ethyl acetate. Purification by combi-flash chromatography (120 g column; eluted with hexanes—Ethyl acetate (5% -25%) in 20 min.; flow rate: 70 mL/min and collected 25 mL/fraction) yielded the title compound as a colorless liquid.

$^1$H NMR (CD3COCD3) δ (ppm): 7.54 (m, 4H), 5.86 (t, 1H), 5.10 (s, 1H), 1.64 (s, 3H).

Step 2: Preparation of N$^1$-(1-cyanocyclopropyl)-N$^2$-{(1S)-1-[4'-(2,2-difluoro-1-hydroxy-1-methylethyl)biphenyl-4-yl]-2,2,2-trifluoroethyl-}-4-fluoro-L-leucinamide The boronate ester of step 3 in example 1 (2.5 g) and the bromide from step 1 in example 9 (1.6 mg) were coupled as in step 4 of example 1 to provide the mixture of diatereomers as a white powder.

Step 3: Separation of diastereomers

The 1:1 diastereomeric mixture from step 2 in example 9 (80 mg) was dissolved in ethanol (2 mL). The mixture of compounds was resolved in ~10 injections (10×200 μL) with a Chiralcel OD semi-preparative column (2 cm I.D.×25 cm) eluting with 32.5% 2-propanol in hexanes and a flow rate of 6 mL/min. The fast fractions eluted at 21-23 min were pooled and concentrated to give N$^1$-(1-cyanocyclopropyl)-N$^2$-((1S)-1-{4'-[(1R)-2,2-difluoro-1-hydroxy-1-methylethyl]biphenyl-4-yl}-2,2,2-trifluoroethyl)-4-fluoro-L-leucinamide as a white powder (98% d.e.). Stereochemistry is tentative.

(MH)$^+$ ESI=542

The slow fraction eluted at ~25 min were pooled and concentrated to give N$^1$-(1-cyanocyclopropyl)-N$^2$-((1S)-1-{4'-[(1S)-2,2-difluoro-1-hydroxy-1-methylethyl]biphenyl-4-yl}-2,2,2-trifluoroethyl)-4-fluoro-L-leucinamide as a white powder (98% d.e.). Stereochemistry is tentative.

(MH)$^+$ ESI=542

EXAMPLE 10

Synthesis of N$^1$-(1-cyanocyclopropyl)-N$^2$-((1S)-1-{4'-[(1S)-2,2-difluoro-1-hydroxy-1-(hydroxymethyl)ethyl]biphenyl-4-yl}-2,2,2-trifluoroethyl)-4-fluoro-L-leucinamide

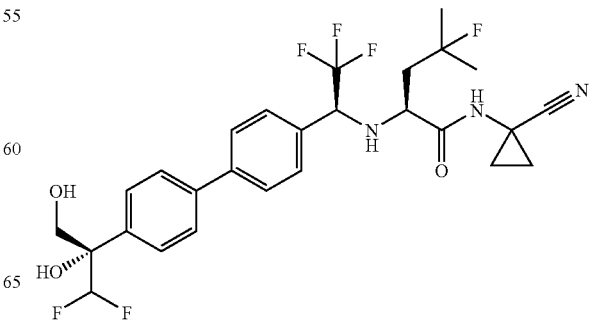

Step 1: Preparation of 1-Bromo-4-[1-(difluoromethyl)vinyl]benzene

To activated zinc dust (13.3 g, 0.2 mol) in a 1 L flask was added THF (200 mL). Diiodomethane (8.9 mL, 110 mmol) was added dropwise over ~10 min. The mixture was stirred at room temperature for 30 min. The mixture was cooled with an ice-acetone bath, a solution of tin(iv) chloride 1M in $CH_2Cl_2$ (22.1 mL, 22.1 mmol) was added over ~15 min (needle tip inserted inside the mixture). The mixture was stirred for 15 min and the cooling bath was removed. The mixture was stirred at r.t for 30 min. After cooling back with an ice-acetone bath, a solution of 1-(4-bromophenyl)-2,2-difluoroethanone (5.2 g, 22.12 mmol) in THF (30 mL) was added dropwise over ~10 min. The cooling bath was removed and the mixture was stirred at room temperature for 30 min. The mixture was then poured portionwise to a mixture of sodium bicarbonate (300 mL, 300 mmol) and hexanes (300 mL) at 0° C. After stirring for 15 min, the mixture was filtered through celite. The organic layer was separated, washed with brine, dried ($Na_2SO_4$) and concentrated. Chromatography over silica gel and elution with hexanes: Ethyl acetate (20:1) gave the title compound as a pale yellow liquid.

$^1$H NMR (CD3COCD3) δ (ppm): 7.60 (d, 2H), 7.50 (d, 2H), 6.70 (t, 1H), 5.92 (s, 1H), 5.80 (s, 1H).

Step 2: Preparation of (2S)-2-(4-bromophenyl)-3,3-difluoropropane-1,2-diol

To a 250 mL flask charged with commercial AD-mix-alpha (7 g) were added tert-butyl alcohol (25 mL) and $H_2O$ (25 mL). The mixture was stirred at room temperature to give 2 clear phases and the low phases appeared yellow orange. After cooling to 0° C., 1-bromo-4-[1-(difluoromethyl)vinyl]benzene (1.1 g, 4.7 mmol) was added at once and the mixture was stirred at approximately 4° C. overnight. A bright yellow mixture resulted. The mixture was kept at 0° C. and solid sodium sulfite (8 g, 64 mmol) was added. The mixture was warmed to room temperature and stirred for 30 min. Ethyl acetate (50 mL) was added and the organic layer was separated. The aqueous layer was extracted with Ethyl acetate (2×10 mL). Combined Ethyl acetate extracts were dried ($Na_2SO_4$) and concentrated. Purification by combi-flash (40 g column; eluted with hexanes—Ethyl acetate (20% -60%) in 25 min.; flow rate: 35 mL/min and collected 18 mL/fraction) yielded the title compound as a colorless oil.

$^1$H NMR (CD3COCD3) δ (ppm): 7.56 (s, 4H), 6.14 (t, 1H), 5.00 (s, 1H), 4.40 (t, 1H), 4.00 (m, 1H), 3.80 (m, 1H).

Step 3: Preparation of $N^1$-(1-cyanocyclopropyl)-$N^2$-((1S)-1-{4'-[(1S)-2,2-difluoro-1-hydroxy-1-(hydroxymethyl)ethyl]biphenyl-4-yl}1-2,2,2-trifluoroethyl)-4-fluoro-L-leucinamide The boronate ester of step 3 in example 1 (900 mg) and the bromide from step 2 in example 10 (450 mg) were coupled as in step 4 of example 1 to provide the title compound as a white powder.

An ester mono-phosphonate derivative (Yves Leblanc, et. al. Tetrahedron Asymmetry 2001, 12, 3063-3066) was prepared for optical purity measurement (94% d.e.; Chiralpak AD, 40% 2-propanol in hexanes, flow rate 1 mL/min; retention time 7.4 min).

$^1$H NMR (CD3COCD3) δ (ppm): 8.15 (s, 1H), 7.70 (m, 6H), 7.55 (d, 2H), 6.20 (t, 1H), 4.92 (s, 1H), 4.35 (m, 2H), 4.08 (m, 1H), 3.85 (m, 1H), 3.52 (m, 1H), 1.98 (m, 2H), 1.50-1.28 (m, 8H), 1.05 (m, 1H), 0.90 (m, 1H).

EXAMPLE 11

Synthesis of $N^1$-(1-cyanocyclopropyl)-$N^2$-((1S)-1-{4'-[(1R)-2,2-difluoro-1-hydroxy-1-(hydroxymethyl)ethyl]biphenyl-4-yl}-2,2,2-trifluoroethyl)-4-fluoro-L-leucinamide

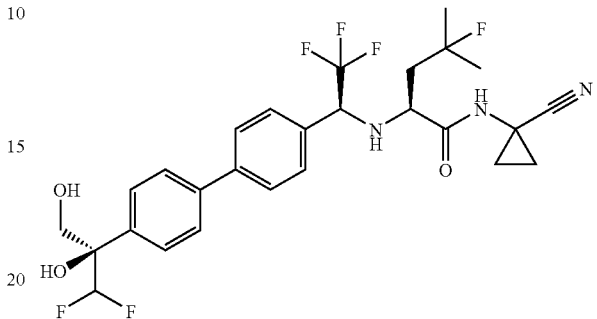

Step 1: Preparation of (2R)-2-(4-bromophenyl)-3,3-difluoropropane-1,2-diol

To a 250 mL flask charged with commercial AD-mix-beta (7 g) were added t-BuOH (25 mL) and $H_2O$ (25 mL). The mixture was stirred at room temperature to give 2 clear phases and the low phases appeared yellow orange. After cooling to 0° C., 1-bromo-4-[1-(difluoromethyl)vinyl]benzene (1.1 g, 4.7 mmol) was added at once and the mixture was stirred at approximately 4° C. overnight. A bright yellow mixture resulted. The mixture was kept at 0° C. and solid sodium sulfite (8 g, 64 mmol) was added. The mixture was warmed to room temperature and stirred for 30 min. Ethyl acetate (50 mL) was added and the organic layer was separated. The aqueous layer was extracted with ethyl acetate (2×10 mL). Combined ethyl acetate extracts were dried ($Na_2SO_4$) and concentrated. Purification by combined Flash (40 g column; eluted with hexanes—Ethyl acetate (20% -60%) in 25 min.; flow rate: 35 mL/min and collected 18 mL/fraction) yielded the title compound as a colorless oil.

$^1$H NMR (CD3COCD3) δ (ppm): 7.56 (s, 4H), 6.14 (t, 1H), 5.00 (s, 1H), 4.40 (t, 1H), 4.00 (m, 1H), 3.80 (m, 1H).

Step 2: Preparation of $N^1$-(1-cyanocyclopropyl)-$N^2$-((1S)-1-{4'-[(1R)-2,2-difluoro-1-hydroxy-1-(hydroxymethyl)ethyl]biphenyl-4-yl}-2,2,2-trifluoroethyl)-4-fluoro-L-leucinamide The boronate ester of step 3 in example 1 (1.5 g) and the bromide from step 1 in example 11 (740 mg) were coupled as in step 4 of example 1 to provide the title compound as a white powder.

An ester mono-phosphonate derivative (Yves Leblanc, et. al. Tetrahedron Asymmetry 2001, 12, 3063-3066) was prepared for optical purity measurement (94% d.e.; Chiralpak AD, 40% 2-propanol in hexanes, flow rate 1 mL/min; retention time 11.1 min).

$^1$H NMR (CD3COCD3) δ (ppm): 8.15 (s, 1H), 7.70 (m, 6H), 7.55 (d, 2H), 6.20 (t, 1H), 4.92 (s, 1H), 4.35 (m, 2H), 4.08 (m, 1H), 3.85 (m, 1H), 3.52 (m, 1H), 1.98 (m, 2H), 1.50-1.28 (m, 8H), 1.05 (m, 1H), 0.90 (m, 1H).

EXAMPLE 12

Synthesis of N²-[(1S)-1-(4-bromophenyl)-2,2,2-trifluoroethyl]-N¹-(1-cyanocyclopropyl)-4-fluoro-L-leucinamide

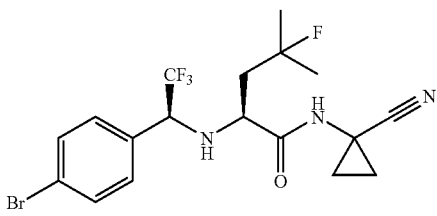

Step 1: Preparation of benzyl (3S)-3-[(tert-butoxycarbonyl)amino]-4-hydroxybutanoate N-(tert-Butoxycarbonyl)-L-aspartic acid 4-benzyl ester (30 g) was dissolved in dimethoxyethane (90 mL) and the solution was cooled to −5° C. N-Methylmorpholine (10.32 mL) was added followed by a slow addition of isobutyl chloroformate (12.66 mL) such that the reaction temperature was kept below −10° C. The mixture was aged for 0.5 hour. The solids were quickly filtered and washed with dimethoxyethane (90 mL). The filtrate was cooled to −50° C. and a solution of sodium borohydride (4.4 g) in water (45 mL) was added slowly such that the reaction temperature was maintained between −30° C. and −15° C. Water (500 mL) was then added such that the reaction mixture temperature was maintained below −15° C. The suspension was filtered, the solid washed with water (400 mL) and dried to yield benzyl (3S)-3-[(tert-butoxycarbonyl)amino]-4-hydroxybutanoate.

¹H NMR (CD$_3$COCD$_3$) δ 7.3-7.45 (5H, m), 5.85-5.95 (1H, NH), 5.15 (2H, s), 3.95-4.1 (2H, m), 3.5-3.7 (2H, m), 2.55-2.75 (2H, m), 1.4 (9H, s).

Step 2: Preparation of benzyl [(4S)-2-oxo-1,3-oxazolidin-4-yl]acetate

To a solution of the alcohol (95.7 g) from Step 1 in dichloroethane (925 mL) was added pyridine (625 mL) and the mixture was cooled to 0-5° C. Anhydrous p-toluenesulfonic anhydride (105.7 g) was added and the mixture was warmed to room temperature and stirred for 1 hour and then heated to 90° C. for 2 hours. The mixture was cooled, diluted with dichloromethane (1000 mL) and washed with 1N HCl (3×600 mL). The organic layer was washed with brine, dried with sodium sulfate and the solvents were removed in vacuo. The residue was purified by chromatography on SiO$_2$ using ethyl acetate and hexanes in a 1:1 ratio followed by ethyl acetate to yield benzyl [(4S)-2-oxo-1,3-oxazolidin-4-yl]acetate.

¹H NMR (CD$_3$SOCD$_3$) δ 7.8 (1H, NH), 7.3-7.45 (5H, m), 5.05-5.15 (2H, m), 4.4-4.5 (1H, m), 4.1-4.2 (1H, m), 4.0-4.05 (1H, m), 3.6-3.8 (2H, m).

Step 3: Preparation of (4S)-4-(2-hydroxy-2-methylpropyl)-1,3-oxazolidin-2-one Methylmagnesium bromide (227 mL of 3M solution in diethyl ether) was added to a mixture of toluene (340 mL) and THF (340 mL) at −20° C. A warm THF solution (170 mL) of the ester from Step 2 (40 g) was then added dropwise maintaining the temperature below −10° C. The mixture was aged for 2 hours and was then slowly added to a mixture of water (1000 mL) and acetic acid (200 mL) and the resultant mixture was stirred for 2 hours at room temperature. The aqueous layer was separated and the organic layer was extracted with water (2×200 mL). The product was extracted from the combined aqueous layers using dichloromethane and a continuous extractor. The dichloromethane extract was evaporated to dryness using heptane as a co-solvent to azeotrope off the acetic acid. The residue was purified by chromatography on SiO$_2$ using ethanol and dichloromethane (1:30) to yield (4S)-4-(2-hydroxy-2-methylpropyl)-1,3-oxazolidin-2-one.

¹H NMR (CD$_3$COCD$_3$) δ 6.1-6.4 (1H, NH), 4.45-4.55 (1H, m), 4.1-4.2 (1H, m), 3.95-4.05 (1H, m), 3.7 (1H, s), 1.65-1.85 (2H, m), 1.25 (6H, m).

Step 4: Preparation of (4S)-4-(2-fluoro-2-methylpropyl)-1,3-oxazolidin-2-one A dichloromethane solution (100 mL) of the alcohol (47.8 g) from Step 3 was added to a −70° C. solution of (diethylamino)sulfur trifluoride (48.5 g) in dichloromethane (500 mL). The mixture was warmed to room temperature and stirred for 1 hour. The mixture was then carefully added to a 0° C. mixture of saturated aqueous NaHCO$_3$ (800 mL). The organic layer was separated and washed with saturated aqueous NaHCO$_3$. The aqueous was further extracted with dichloromethane (100 mL) and the combined dichloromethane layers were dried and concentrated. The residue was purified by chromatography on SiO$_2$ using ethyl acetate and hexanes (1:5) followed by ethyl acetate to yield (4S)-4-(2-fluoro-2-methylpropyl)-1,3-oxazolidin-2-one.

¹H NMR (CD$_3$SOCD$_3$) δ 7.6 (1H, NH), 4.4-4.5 (1H, m), 3.95-4.05 (1H, m), 3.9-3.95 (1H, m), 1.8-1.95 (2H, m), 1.25-1.4 (6H, 2s).

Step 5: Preparation of (2S)-2-amino-4-fluoro-4-methylpentan-1-ol

To a solution of the fluoro derivative (21.0 g) from Step 4 in 90% aqueous ethyl alcohol (216 mL) was added potassium hydroxide (21.9 g). The mixture was heated at reflux for 4 hours and cooled to room temperature. The mixture was then concentrated and co-evaporated with toluene (3×300 mL). The residue was dissolved in dichloromethane (500 mL) and stirred for 0.5 hour. The suspension was filtered through celite and the celite was washed with dichloromethane (3×100 mL). The filtrate was concentrated to dryness to yield (2S)-2-amino-4-fluoro-4-methylpentan-1-ol.

¹H NMR (CD$_3$OD) δ 3.4-3.5 (1H, m), 3.2-3.3 (1H, m), 3.0-3.1 (1H, m), 1.5-1.7 (2H, m), 1.35 (3H, s), 1.3 (3H, s).

Step 6: Preparation of (2S)-1-{[tert-butyl(dimethyl)silyl]oxy}-4-fluoro-4-methylpentan-2-amine The amino alcohol (21.0 g) from Step 5 was dissolved in dichloromethane (300 mL) and the solution was cooled to 0° C. 4-(Dimethylamino)pyridine (0.051 g) and tert-butyldimethylsilyl chloride (21 g) were added followed by triethylamine (25 mL). The mixture was stirred at room temperature overnight. The reaction mixture was slowly poured into 0° C. saturated aqueous ammonium chloride and extracted with dichloromethane (3×300 mL). The organic layer was washed with brine, dried with sodium sulfate and the solvents were removed in vacuo to yield (2S)-1-{[tert-butyl(dimethyl)silyl]oxy}-4-fluoro-4-methylpentan-2-amine.

¹H NMR (CD$_3$OD) δ 3.6-3.65 (1H, m), 3.4-3.5 (1H, m), 3.1-3.2 (1H, m), 1.6-1.8 (2H, m), 1.35-1.45 (6H, m), 0.93 (9H, s), 0.1 (6H, s).

Step 7: Preparation of (2S)-1-{[tert-butyl(dimethyl) silyl]oxy}-4-fluoro-4-methyl-N-[(1E)-2,2,2-trifluoroethylidene]pentan-2-amine To a solution of the amine (31.5 g) from Step 6 in benzene (126 mL) was added trifluoroacetaldehyde methyl hemiacetal (21.6 mL.). The solution was heated at reflux overnight using a Dean-Stark trap to collect water. The reaction mixture was cooled to room temperature and concentrated to dryness. The residue was purified on $SiO_2$ using 4% of ethyl acetate in hexanes to yield (2S)-1-{[tert-butyl(dimethyl)silyl]oxy}-4-fluoro-4-methylpentan-2-amine.

$^1$H NMR ($CD_3COCD_3$) δ 7.9-7.95 (1H, m), 3.75-3.85 (1H, m), 3.7-3.75 (1H, m), 3.53-3.6 (1H, m), 1.9-2.0 (2H, m), 1.3-1.4 (6H, m), 0.9 (9H, s), 0.1 (3H, s), 0.05 (3H, s).

Step 8: Preparation of (2S)-2-{[(1S)-1-(4-bromophenyl)-2,2,2-trifluoroethyl]amino}-4-fluoro-4-methyl-pentan-1-ol To a −75° C. solution of 1,4-dibromobenzene (0.26 g) in THF (4 mL) was added n-BuLi (0.42 mL of a 2.5M hexanes solution) and the mixture was aged for 20 minutes. The imine (0.329 g) from Step 7 in THF (2 mL) was added and the mixture was aged 2 hours. The mixture was then added to a mixture of water (50 mL), $NH_4Cl$ (1 g) and crushed ice. It was extracted with ethyl acetate (2×25 mL) and the combined ethyl acetate layers were dried and evaporated to dryness.

The same procedure was repeated on a larger scale using 1,4-dibromobenzene (1.2 g), n-BuLi (1.84 mL) and the imine (1.38 g) and the reaction mixture was treated as above. The combined residues from both preparations were dissolved in THF (10 mL) and cooled to 0° C. n-Tetrabutylammonium fluoride (6 mL from a 1M THF solution) was added and the mixture was stirred at +5° C. for 16 h. The mixture was poured into a mixture of water (50 mL), ammonium chloride (1 g) and crushed ice and the organic layer was separated. The aqueous was further extracted with ethyl acetate (2×15 mL) and the combined organic layers were dried and concentrated. The residue was purified on $SiO_2$ using ethyl acetate and hexanes (1:5) to yield (2S)-2-{[(1S)-1-(4-bromophenyl)-2,2,2-trifluoroethyl]amino}-4-fluoro-4-methylpentan-1-ol.

$^1$H NMR ($CD_3COCD_3$) δ 7.65 (2H, m), 7.5 (2H, m), 4.5-4.6 (1H, m), 3.8 (1H, m), 3.6 (1H, m), 3.3-3.4 (1H, m), 2.85-2.0 (1H, m), 2.55 (1H, m), 1.7-1.9 (2H, s), 1.3-1.4 (6H, m).

Step 9: Preparation $N^2$-[(1S)-1-(4-bromophenyl)-2,2,2-trifluoroethyl]-$N^1$-(1-cyanocyclopropyl)-4-fluoro-L-leucinamide A suspension of $H_5IO_6/CrO_3$ (66 mL of 0.44 M in $CH_3CN$; Note) was cooled to 0° C. and a solution of the alcohol from Step 8 (1.55 g) in $CH_3CN$ (5 mL) was added dropwise. The mixture was stirred at 0-5° C. for 3.5 hours. It was poured into pH 4 $Na_2HPO_4$ (200 mL) under vigorous stirring and the mixture was extracted with diethyl ether (3×50 mL). The combined ether extracts were washed with water and brine (1:1) followed by dilute aqueous $NaHSO_3$ and brine. The mixture was dried with sodium sulfate, filtered and the solvents were evaporated to dryness to yield of N-[(1S)-1-(4-bromophenyl)-2,2,2-trifluoroethyl]-4-fluoro-L-leucine which was used as such in the next step.

Note. The oxidizing reagent ($H_5IO_6/CrO_3$) was prepared as described in Tetrahedron Letters 39 (1998) 5323-5326 but using HPLC grade $CH_3CN$ (contains 0.5% water); no water was added.

Diisopropylethylamine (4.2 mL) was added to a 0° C. suspension of the acid (1.5 g) from above, 1-amino-1-cyclopropanecarbonitrile hydrochloride (1.18 g), O-(7-azabenzotriazol-1-yl)-N,N,N',N'-tetramethyluronium hexafluorophosphate (1.94 g) and dimethylformamide (5 mL) and the mixture was reacted at room temperature for 48 h. It was then poured on ice and dilute aqueous ammonium chloride. The mixture was extracted with ethyl acetate and ether (1:1) and the combined organic layers were washed with pH 3 dilute $Na_2HPO_4$ and brine. The solvents were evaporated to dryness and the residue was purified by chromatography on $SiO_2$ using ethyl acetate and hexanes (1:2) to yield $N^2$-[(1S)-1-(4-bromophenyl)-2,2,2-trifluoroethyl]-$N^1$-(1-cyanocyclopropyl)-4-fluoro-L-leucinamide in a sufficient purity state for the next step.

$^1$H NMR ($CD_3COCD_3$) δ 8.15 (1H, NH), 7.6 (2H, m), 7.45 (2H, m), 4.35-4.45 (1H, m), 3.45-3.55 (1H, m), 1.9-2.1 (2H, m), 1.75-1.85 (1H, NH), 1.35-1.55 (8H, m), 1.1-1.15 (1H, m), 0.95-1.05 (1H, m).

Pharmaceutical Composition

As a specific embodiment of this invention, 100 mg of (1R,2R)-N-(cyanomethyl)-5,5-difluoro-2-[4'-(methylthio)-1,1'-biphenyl-2-yl]cyclohexanecarboxamide, is formulated with sufficient finely divided lactose to provide a total amount of 580 to 590 mg to fill a size 0, hard-gelatin capsule.

The compounds disclosed in the present application exhibited activity in the following assays. In addition, the compounds disclosed in the present application have an enhanced pharmacological profile relative to previously disclosed compounds.

Cathepsin K Assay

Serial dilutions (⅓) from 500 μM down to 0.0085 μM of test compounds were prepared in dimethyl sulfoxide (DMSO). Then 2 μL of DMSO from each dilution were added to 50 μL of assay buffer (MES, 50 mM (pH 5.5); EDTA, 2.5 mM; DTT, 2.5 mM and 10% DMSO) and 25 μL of human cathepsin K (0.4 nM) in assay buffer solution. The assay solutions were mixed for 5-10 seconds on a shaker plate and incubated for 15 minutes at room temperature. Z-Leu-Arg-AMC (8 μM) in 25 μL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathepsin L Assay

Serial dilutions (⅓) from 500 μM down to 0.0085 μM of test compounds were prepared in dimethyl sulfoxide (DMSO). Then 2 μL of DMSO from each dilution were added to 50 μL of assay buffer (MES, 50 mM (pH 5.5); EDTA, 2.5 mM; DTT, 2.5 mM and 10% DMSO) and 25 μL of human cathepsin L (0.5 nM) in assay buffer solution. The assay solutions were mixed for 5-10 seconds on a shaker plate and incubated for 15 minutes at room temperature. Z-Leu-Arg-AMC (8 μM) in 25 μL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathepsin B Assay

Serial dilutions (⅓) from 500 μM down to 0.0085 μM of test compounds were prepared in dimethyl sulfoxide (DMSO). Then 2 μL of DMSO from each dilution were added to 50 μL of assay buffer (MES, 50 mM (pH 5.5); EDTA, 2.5 mM; DTT, 2.5 mM and 10% DMSO) and 25 µL of human cathepsin B (4.0 nM) in assay buffer solution. The assay solutions were mixed for 5-10 seconds on a shaker plate and incubated for 15 minutes at room temperature. Z-Leu-Arg-AMC (8 µM) in 25 µL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathepsin S Assay

Serial dilutions (⅓) from 500 µM down to 0.0085 µM of test compounds were prepared in dimethyl sulfoxide (DMSO). Then 2 µL of DMSO from each dilution were added to 50 µL of assay buffer (MES, 50 mM (pH 5.5); EDTA, 2.5 mM; DTT, 2.5 mM and 10% DMSO) and 25 µL of human cathepsin S (20 nM) in assay buffer solution. The assay solutions were mixed for 5-10 seconds on a shaker plate and incubated for 15 minutes at room temperature. Z-Leu-Arg-AMC (8 µM) in 25 µL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Pharmacokinetics in Rats

Per Os (PO) Pharmacokinetics in Rats

Procedure:

The animals are housed, fed and cared for according to the Guidelines of the Canadian Council on Animal Care.

Male Sprague Dawley rats (250-400 g) are fasted overnight prior to each PO blood level study.

The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 0.5 mL of blood is collected into a heparinized vacutainer tube.

Compounds are prepared as required, in a standard dosing volume of 10 mL/kg, and administered orally by passing a 16 gauge, 3" gavaging needle into the esophagus.

Subsequent blood collections are taken in the same manner as the zero blood sample except that there is no need to nick the tail again. The tail is cleaned with a piece of gauze and milked/stroked as described above into the appropriately labeled tubes.

Immediately after sampling, blood is centrifuged, separated, the plasma put into clearly marked vials and stored in a freezer until analyzed.

Typical time points for determination of rat blood levels after PO dosing are:

0, 15 min, 30 min, 1 h, 2 h, 4 h, 6 h, 8 h, 24 h

After the 4 hr time point bleed, food is provided to the rats ad libitum. Water is provided at all times during the study.

Vehicles:

The following vehicles (with corresponding dose volumes) may be used in PO rat blood level determinations:

| | |
|---|---|
| PEG 200/300/400 (0-60% in water): | equal or less than 10 mL/kg |
| Methocel (0.5%-1.0% in water): | equal or less than 10 mL/kg |
| Tween 80 (1-10% in water): | equal or less than 10 mL/kg |

Compounds for PO blood levels can be in suspension form. For better homogeneity, the suspension can be placed in a sonicator for approximately 5 minutes.

For analysis, aliquots are diluted with 1.2 to 1.5 volumes of acetonitrile optionally containing an internal standard and centrifuged to remove protein precipitate. The supernatant is injected directly onto a C-18 HPLC column with mass spectrometry (MS) or ultra-violet absorbance (UV) or fluorescence (Fluo) detection. Quantization is done relative to a standard curve prepared using clean blood samples spiked with a known quantities of drug in acetonitrile optionally containing an internal standard. Additional acetonitrile optionally containing internal standard is added to amount 1.2 to 1.5 volumes of the initial blood amount to correspond to what was done in the case of the samples. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

and $$AUC = (C1 + C2) * (T2 - T1)/2$$

where C is the measured concentration by MS or UV or Fluo at a given time T

Intravenous Pharmacokinetics in Rats

Procedure:

The animals are housed, fed and cared for according to the Guidelines of the Canadian Council on Animal Care.

Male Sprague Dawley (325-375 g) non-fasted rats are used in theses studies.

The compound is prepared as required, in a standard dosing volume of 1 mL/kg.

Dosing of the conscious rats for intravenous administration is done via the jugular vein using a 25 gauge needle. This constitutes the zero time point.

The 5 min bleed is taken by nicking a piece (1-2 mm) off the tip of the tail. The tail is then stroked with a firm but gentle motion from the top of the tail to the bottom to milk the blood out of the tail. Approximately 0.5 mL of blood is collected into a heparinized collection vial. Subsequent bleeds are taken in the same fashion, except that there is no need to nick the tail again. The tail is cleaned with a piece of gauze and bled, as described above, into the appropriate labeled tubes.

Typical time points for determination of rat blood levels after I.V. dosing are either:

0, 5 min, 5 min, 30 min, 1 h, 2 h, 4 h, 6 h or 0, 5 min, 30 min, 1 h, 2 h, 4 h, 6 h, 8 h, 24 h Vehicles:

The following vehicles may be used in IV rat blood level determinations:

| | |
|---|---|
| Dextrose: | 1 mL/kg |
| Moleculosol 25%: | 1 mL/kg |
| DMSO (dimethylsulfoxide): | Restricted 10% of the dose volume up to 0.1 mL per kilogram of animal |
| PEG 200: | Not more than 80% mixed with 20% sterile water - 1 mL/kg |

With Dextrose, either sodium bicarbonate can be added if the solution is cloudy.

For analysis, aliquots are diluted with 1.2 to 1.5 volumes of acetonitrile optionally containing an internal standard and centrifuged to remove protein precipitate. The supernatant is injected directly onto a C-18 HPLC column with mass spectrometry (MS) or ultra-violet absorbance (UV) or fluorescence (Fluo) detection. Quantization is done relative to a standard curve prepared using clean blood samples spiked with a known quantities of drug in acetonitrile optionally containing an internal standard. Additional acetonitrile optionally containing internal standard is added to amount 1.2 to 1.5 volumes of the initial blood amount to correspond to what was done in the case of the samples. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

and $$AUC = (C1 + C2)*(T2 - T1)/2$$

where C is the measured concentration by MS or UV or Fluo at a given time T.

What is claimed is:

1. A compound of the formula:

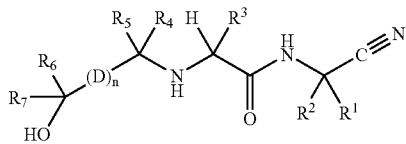

wherein $R^1$ and $R^2$ are taken together with the carbon atom to which they are attached to form a $C_{3-4}$ cycloalkyl which is optionally substituted with $C_{1-3}$ alkyl;

$R^3$ is $C_{1-6}$ alkyl which is substituted with one to four fluoro or one to four chloro;

$R^4$ is $C_{1-6}$ alkyl which is substituted with one to five halo;

$R^5$ is hydrogen or $C_{1-6}$ alkyl which is optionally substituted with one to five halo;

each D is independently aryl or heteroaryl;

$R^6$ is hydrogen or $C_{1-6}$ alkyl which is optionally substituted with one to two hydroxyl or two to six halo;

$R^7$ is $C_{1-6}$ alkyl which is optionally substituted with two to five halo;

n is two;

or a pharmaceutically acceptable salt or stereoisomer thereof.

2. The compound of claim 1 wherein $R^1$ and $R^2$ are taken together with the carbon atom to which they are attached to form cyclopropyl; or a pharmaceutically acceptable salt or stereoisomer thereof.

3. The compound of claim 2 wherein D is phenyl; or a pharmaceutically acceptable salt or stereoisomer thereof.

4. The compound of claim 3 wherein $R^5$ is hydrogen and $R^4$ is $CF_3$; or a pharmaceutically acceptable salt or stereoisomer thereof.

5. The compound of claim 4 wherein $R^7$ is $C_{1-3}$ alkyl substituted with two or three fluoro; or a pharmaceutically acceptable salt or stereoisomer thereof.

6. The compound of claim 1 which is:

$N^1$-(1-cyanocyclopropyl)-$N^2$-(1-{4'-[2,2-difluoro-1-hydroxyethyl]biphenyl-4-yl}-2,2,2-trifluorethyl)-4-fluoro-L-leucinamide;

$N^1$-(1-cyanocyclopropyl)-4-fluoro-$N^2$-{2,2,2-trifluoro-1-[4'-(2,2,2-trifluoro-1-hydroxyethyl)biphenyl-4-yl]ethyl}-L-leucinamide;

$N^1$-(1-cyanocyclopropyl)-4-fluoro-$N^2$-(2,2,2-trifluoro-1-{4'-[3,3,3-trifluoro-1-hydroxy-1-methylpropyl]biphenyl-4-yl}ethyl)-L-leucinamide;

$N^1$-(1-cyanocyclopropyl)-4-fluoro-$N^2$-(2,2,2-trifluoro-1-{4'-[2,2,2-trifluoro-1-hydroxy-1-(trifluoromethyl)ethyl]biphenyl-4-yl}ethyl)-L-leucinamide;

$N^1$-(1-cyanocyclopropyl)-4-fluoro-$N^2$-{2,2,2-trifluoro-1-[4'-(2,2,2-trifluoro-1-hydroxy-1-methylethyl)biphenyl-4-yl]ethyl}-L-leucinamide;

$N^1$-(1-cyanocyclopropyl)-4-fluoro-$N^2$-(2,2,2-trifluoro-1-{4'-[1-hydroxy-1-(trifluoromethyl)propyl]biphenyl-4-yl}ethyl)-L-leucinamide;

$N^1$-(1-cyanocyclopropyl)-$N^2$-(1-{4'-[2,2-difluoro-1-hydroxy-1-methylethyl]biphenyl-4-yl}-2,2,2-trifluoroethyl)-4-fluoro-L-leucinamide;

$N^1$-(1-cyanocyclopropyl)-$N^2$-(1-{4'-[2,2difluoro-1-hydroxy-1-(hydroxymethyl)ethyl]biphenyl-4-yl}-2,2,2-trifluoroethyl)-4-fluoro-L-leucinamide;

$N^2$-[1-(4-bromophenyl)-2,2,2-trifluoroethyl]-$N^1$-(1-cyanocyclopropyl)-4-fluoro-L-leucinamide;

or a pharmaceutically acceptable salt or stereoisomers thereof.

7. The compound of claim 6 which is:

$N^1$-(1-cyanocyclopropyl)-$N^2$-((1S)-1-{4'-[(1R)-2,2-difluoro-1-hydroxyethyl]biphenyl-4-yl}-2,2,2-trifluoroethyl)-4-fluoro-L-leucinamide;

$N^1$-(1-cyanocyclopropyl)-$N^2$-((1S)-1-{4'-[(1S)-2,2-difluoro-1-hydroxyethyl]biphenyl-4-yl}-2,2,2-trifluoroethyl)-4-fluoro-L-leucinamide;

$N^1$-(1-cyanocyclopropyl)-4-fluoro-$N^2$-{(1S)-2,2,2-trifluoro-1-[4'-(2,2,2-trifluoro-1-hydroxyethyl)biphenyl-4-yl]ethyl}-L-leucinamide;

$N^1$-(1-cyanocyclopropyl)-4-fluoro-$N^2$-((1S)-2,2,2-trifluoro-1-{4'-[(1S)-3,3,3-trifluoro-1-hydroxy-1-methylpropyl]biphenyl-4-yl}ethyl)-L-leucinamide;

$N^1$-(1-cyanocyclopropyl)-4-fluoro-$N^2$-((1S)-2,2,2-trifluoro-1-{4'-[(1R)-3,3,3-trifluoro-1-hydroxy-1-methylpropyl]biphenyl-4-yl}ethyl)-L-leucinamide;

$N^1$-(1-cyanocyclopropyl)-4-fluoro-$N^2$-{(1S)-2,2,2-trifluoro-1-[4'-(R)-(2,2,2-trifluoro-1-hydroxyethyl)biphenyl-4-yl]ethyl}-L-leucinamide;

$N^1$-(1-cyanocyclopropyl)-4-fluoro-$N^2$-((1S)-2,2,2-trifluoro-1-{4'-[2,2,2-trifluoro-1-(trifluoromethyl)ethyl]biphenyl-4-yl}ethyl)-L-leucinamide;

$N^1$-(1-cyanocyclopropyl)-4-fluoro-$N^2$-{(1S)-2,2,2-trifluoro-1-[4'-(2,2,2-trifluoro-1-hydroxy-1-methylethyl)biphenyl-4-yl]ethyl}-L-leucinamide;

$N^1$-(1-cyanocyclopropyl)-4-fluoro-$N^2$-((1S)-2,2,2-trifluoro-1-{4'-[1-hydroxy-1-(trifluoromethyl)propyl]biphenyl-4-yl}ethyl)-L-leucinamide;

$N^1$-(1-cyanocyclopropyl)-$N^2$-((1S)-1-{4'-[(1R)-2,2-difluoro-1-hydroxy-1-methylethyl]biphenyl-4-yl}-2,2,2-trifluoroethyl)-4-fluoro-L-leucinamide;

$N^1$-(1-cyanocyclopropyl)-$N^2$-((1S)-1-{4'-[(1S)-2,2-difluoro-1-hydroxy-1-methylethyl]biphenyl-4-yl}-2,2,2-trifluoroethyl)-4-fluoro-L-leucinamide;

$N^1$-(1-cyanocyclopropyl)-$N^2$-((1S)-1-{4'-[(1S)-2,2-difluoro-1-hydroxy-1-(hydroxymethyl)ethyl]biphenyl-4-yl}-2,2,2-trifluoroethyl)-4-fluoro-L-leucinamide;

N¹-(1-cyanocyclopropyl)-N²-((1S)-1-{4'-[(1R)-2,2-difluoro-1-hydroxy-1-(hydroxymethyl)ethyl]biphenyl-4-yl}-2,2,2-trifluoroethyl)-4-fluoro-L-leucinamide;

N²-[(1S)-1-(4-bromophenyl)-2,2,2-trifluoroethyl]-N¹-(1-cyanocyclopropyl)-4-fluoro-L-leucinamide;

or a pharmaceutically acceptable salt, stereoisomers or N-oxide derivative thereof.

8. A pharmaceutical composition comprising a compound according to claim 1 and a pharmaceutically acceptable carrier.

9. A pharmaceutical composition comprising a compound of claim 1 and another agent selected from the group consisting of: an organic bisphosphonate, an estrogen receptor modulator, an estrogen receptor beta modulator, an androgen receptor modulator, an inhibitor of osteoclast proton ATPase, an inhibitor of HMG-CoA reductase, an integrin receptor antagonist, or an osteoblast anabolic agent, Vitamin D, a synthetic Vitamin D analogue, a Nonsteroidal anti-inflammatory drug, a selective cyclooxygenase-2 inhibitor, an inhibitor of interleukin-1 beta, a LOX/COX inhibitor, a RANKL inhibitor, and the pharmaceutically acceptable salts and mixtures thereof.

* * * * *